US009128090B2

(12) United States Patent
Lee et al.

(10) Patent No.: US 9,128,090 B2
(45) Date of Patent: Sep. 8, 2015

(54) RAPID WAY TO OBTAIN HIGH EXPRESSION CLONES OF MAMMALIAN CELLS USING A METHYLCELLULOSE AND IMMUNOPRECIPITATION SCREENING METHOD

(75) Inventors: Chichang Lee, Norristown, PA (US); Celia Ly, Downingtown, PA (US); Gordon Moore, Wayne, PA (US)

(73) Assignee: Janssen Biotech, Inc., Horsham, PA (US)

( * ) Notice: Subject to any disclaimer, the term of this patent is extended or adjusted under 35 U.S.C. 154(b) by 2293 days.

(21) Appl. No.: 10/928,815

(22) Filed: Aug. 27, 2004

(65) Prior Publication Data

US 2005/0118652 A1 Jun. 2, 2005

Related U.S. Application Data

(60) Provisional application No. 60/498,828, filed on Aug. 29, 2003.

(51) Int. Cl.
*C12Q 1/68* (2006.01)
*G01N 21/82* (2006.01)
*C07K 16/00* (2006.01)
*G01N 33/569* (2006.01)
*C07K 16/24* (2006.01)

(52) U.S. Cl.
CPC ........ *G01N 33/56966* (2013.01); *C07K 16/241* (2013.01); *C07K 2317/24* (2013.01)

(58) Field of Classification Search
None
See application file for complete search history.

(56) References Cited

U.S. PATENT DOCUMENTS

| 4,950,592 A | 8/1990 | Daiss |
| 6,200,560 B1 * | 3/2001 | Couto et al. ................. 424/93.2 |
| 6,509,166 B1 | 1/2003 | Edberg |

OTHER PUBLICATIONS

Pearson et al, Methods for derivation and detection of anti-parasite monoclonal antibodies. J Immunol Methods 34: 141-154, 1980.*
Miller et al, Monoclonal Antibody Production, Mini Review, downloaded from the web May 29, 2007.*
Datasheet STAR17B, AbD serotec, downloaded May 30, 2008.*
AbD serotec, Datasheet: STAR17B, downloaded May 30, 2008.*

* cited by examiner

*Primary Examiner* — Maria Marvich
(74) *Attorney, Agent, or Firm* — Brian C. Carey

(57) ABSTRACT

The invention provides a genetic screening method for identifying a transfected cell expressing the polypeptide of interest. The methods allows for high throughput screening of recombinant cells for elevated levels of expression of the polypeptide of interest. The invention also provides capture media, formulations and methods of making and using thereof.

15 Claims, 1 Drawing Sheet

RAPID WAY TO OBTAIN HIGH EXPRESSION CLONES OF MAMMALIAN CELLS USING A METHYLCELLULOSE AND IMMUNOPRECIPITATION SCREENING METHOD

This application claims priority to U.S. provisional application Ser. No. 60/498,828, filed on Aug. 29, 2003. The contents of provisional application Ser. No. 60/498,828 are incorporated by reference herein.

BACKGROUND OF THE INVENTION

1. Field of the Invention

The present invention pertains to genetic screening methods, related cells and culturing media thereof, useful in identifying clones of mammalian cells expressing the polypeptide of interest. The methods allows for high throughput screening of recombinant cells for elevated levels of expression of polypeptide of interest. The present invention also provides a screening method useful in screening and isolating clones of mammalian cells expressing high levels of immunoglobulin.

2. Related Background

Recombinant proteins (r-proteins) are an emerging class of therapeutic agents. To obtain a stable clone for recombinant protein production usually requires the transfection of cells with an expression vector containing gene of interest and a dominant genetic marker. Typically, for the selection of stable transfectants, a selectable marker such as an antibiotic resistance gene is transfected along with the target gene of interest. Selection is then carried out in the presence of the specific antibiotic. Cells that have taken up the expression vector DNA survive in appropriate selection media.

Currently, cloning of stably transfected cells relies on performing a series of limiting dilution procedures, a time consuming and labor-intensive process. For example, many commonly used mammalian expression systems are based on stably transfected Chinese Hamster Ovary (CHO) cells and transfection efficiencies in this system range from 10-60% of cells taking up the vector DNA. However, a wide variation in recombinant gene expression exists among clones that stably incorporate the foreign DNA into the genome due to the position effect by which different regions of the chromosome modulate the expression of the transfected gene. Many hundreds, even thousands of transfected clones are typically screened for random high producers because of the random variation in recombinant protein production. Therefore in many cases, screening for high producers has been one of the rate limiting procedures in developing of cell lines expressing r-proteins due to the huge amount of cells to screen and the complicated assays to perform.

Soluble proteins interact with their corresponding antibody to form a precipitate in solid or semisolid substrates such as agarose. One such application is the immunoplate assay used to detect mouse myeloma mutants. Briefly, cells are cloned in soft agarose over feeder layers that undergo contact inhibition. Antibody or antigen reactive with the immunoglobulin that is secreted by the cloned cells is added to the plate and diffuses through the agarose forming an antigen-antibody precipitate surrounding the clone. This precipitate appears as a collection of dark granules and specks under low or medium power with an inverted microscope. This assay was used not only to look for mutants of hybridoma and myeloma cells, but also to clone hybridomas and identify subclones producing the desired antibody. It can also be used to identify high producers.

However, several difficulties were reported previously when using this semi-solid agarose technique for screening clones producing the desired antibody. For example, poor growth of mammalian cells is caused by inability to utilize the correct temperature to seed cells while agarose is cooling. Another common problem is the difficulty in viewing the precipitate in the agarose media even under a microscope. It is also difficult to correlate the precipitate size to the level of protein secretion.

Accordingly, there is a need to provide improved and/or modified screening methods, which overcome and/or substantially ameliorate one or more of these and other problems known in the art.

BRIEF DESCRIPTION OF THE DRAWINGS

FIG. 1 is a representative showing of a halo-producing NSO cell.

SUMMARY OF THE INVENTION

The present invention relates to genetic screening methods, related cells and culturing media thereof, useful in identifying and/or characterizing clones of mammalian cells expressing the polypeptide of interest. The methods allow for high throughput screening of recombinant cells for elevated levels of expression of polypeptide of interest.

In one embodiment, the present invention provides a method for selecting high expression cell clones expressing a polypeptide of interest, comprising: (a) selecting high expression cell clones among cells cultured in a semi-solid culture medium and expressing said polypeptide of interest, wherein said cells are contacted with a capture molecule that interacts with the polypeptide of interest such that said interaction indicates relative expression of said polypeptide for each cell or group of cells. In addition, the present invention further relates to a cell clone identified by such a method.

The cells may be any cell type including prokaryotic and eukaryotic cells. Prokaryotic cells may include but are not limited to bacterial cells or blue-green algae cells. Eukaryotic cells may include but are not limited to mammalian cells, yeast cells or insect cells. Preferably, the cells are eukaryotic cells. In a preferred embodiment, suitable cell lines that can be used according to the present invention include any transformed or immortalized mammalian cell line. Such cell lines include myeloma cell lines, such as Sp2/0, NSO, NS1, CHO, BHK, Ag653, P3X63Ag8.653 cells (ATCC Accession Number CRL-1580) and SP2/0-Ag14 cells (ATCC Accession Number CRL-1851), COS-1 (e.g., ATCC CRL 1650), COS-7 (e.g., ATCC CRL-1651), HEK293, BHK21 (e.g., ATCC CAL-10), CHO (e.g., ATCC CRL 1610, CHO DXB-11, CHO DG44), BSC-1 (e.g., ATCC CAL-26) cell lines, HepG2 cells, P3X63Ag8.653, 293 cells, HeLa cells, NIH 3T3, CDS-1, CDS-7, NIH 273, and the like, or any cells derived therefrom, including cell fusions of the above, such as to protein producing cells, such as B-cells, antibody producing cells, isolated or cloned spleen or lymph node cells, and the like.

The present invention further provides a method of isolating a polypeptide of interest comprising, in addition to above mentioned step (a), harvesting and culturing the cell clones; and isolating the polypeptide of interest therefrom. Moreover, the present invention further relates to at least one polypeptide of interest isolated by such a method.

The polypeptide of interest may be any suitable soluble or membrane-bound polypeptide including, for example but not limited to, an antibody, a growth factor, a hormone, a biopharmaceutical, a receptor or a synthetic polypeptide of interest or portions thereof.

In a preferred embodiment, the polypeptide of interest is a diagnostic or a therapeutic protein. The diagnostic or therapeutic protein may be an immunoglobulin, a cytokine, an integrin, an antigen, a growth factor, a receptor or fusion protein thereof, any fragment thereof, or any structural or functional analog thereof. The diagnostic or therapeutic protein may also be a cell cycle protein, a hormone, a neurotransmitter, a blood protein, an antimicrobial, any fragment thereof, or any structural or functional analog thereof.

In a preferred embodiment, the cell clones selected using the method of the present invention may produce an immunoglobulin or fragment thereof derived from a rodent or a primate. Alternatively, the immunoglobulin or fragment thereof may be chimeric or engineered. Indeed, the present invention further contemplates methods of identifying cell clones that express an immunoglobulin or fragment thereof which is humanized, CDR grafted, phage displayed, transgenic mouse-produced, optimized, mutagenized, randomized or recombined.

The immunoglobulin or fragment thereof may include, but not limited to, IgG1, IgG2, IgG3, IgG4, IgA1, IgA2, IgD, IgE, IgM, and any structural or functional analog thereof. In a specific embodiment, the immunoglobulin expressed in the cells, cell lines, and cell cultures of the present invention is infliximab. Furthermore, the immunoglobulin fragment isolated using the method of the present invention may include, but is not limited to, $F(ab')_2$, Fab', Fab, Fc, Facb, Fc', Fd, Fv and any structural or functional analog thereof. In a specific embodiment, the immunoglobulin fragment is abciximab.

The polypeptide of interest may further include, but not limited to an antigen, a cytokine, an integrin, an antigen, a growth factor, a hormone, a neurotransmitter, a receptor or fusion protein thereof, a blood protein, an antimicrobial, any fragment thereof, and any structural or functional analog of any of the foregoing.

In one embodiment of the present invention, the polypeptide of interest is an integrin. Examples of integrins contemplated by the present invention include, but are not limited to, $\alpha 1$, $\alpha 2$, $\alpha 3$, $\alpha 4$, $\alpha 5$, $\alpha 6$, $\alpha 7$, $\alpha 8$, $\alpha 9$, $\alpha D$, $\alpha L$, $\alpha M$, $\alpha V$, $\alpha X$, $\alpha IIb$, $\alpha IELb$, $\beta 1$, $\beta 2$, $\beta 3$, $\beta 4$, $\beta 5$, $\beta 6$, $\beta 7$, $\beta 8$, $\alpha 1\beta 1$, $\alpha 2\beta 1$, $\alpha 3\beta 1$, $\alpha 4\beta 1$, $\alpha 5\beta 1$, $\alpha 6\beta 1$, $\alpha 7\beta 1$, $\alpha 8\beta 1$, $\alpha 9\beta 1$, $\alpha 4\beta 7$, $\alpha 6\beta 4$, $\alpha D\beta 2$, $\alpha L\beta 2$, $\alpha M\beta 2$, $\alpha V\beta 3$, $\alpha V\beta 5$, $\alpha V\beta 6$, $\alpha V\beta 8$, $\alpha X\beta 2$, $\alpha IIb\beta 3$, $\alpha IELb\beta 7$, and any structural or functional analog thereof.

In an embodiment of the present invention, the polypeptide of interest is an antigen. The antigen may be derived from a number of sources including, but not limited to, a bacterium, a virus, a blood protein, a cancer cell marker, a prion, a fungus, and any structural or functional analog thereof.

In yet another embodiment, the polypeptide of interest is a growth factor. Examples of the growth factors contemplated by the present invention include, but are not limited to, a human growth factor, a platelet derived growth factor, an epidermal growth factor, a fibroblast growth factor, a nerve growth factor, a chorionic gonadotropin, an erythrpoeitin, an activin, an inhibin, a bone morphogenic protein, a transforming growth factor, an insulin-like growth factor, and any structural or functional analog thereof.

In yet another embodiment, the polypeptide of interest is a cytokine. Examples of cytokines contemplated by the present invention include, but are not limited to, an interleukin, an interferon, a colony stimulating factor, a tumor necrosis factor, an adhesion molecule, an angiogenin, an annexin, a chemokine, and any structural or functional analog thereof.

In another embodiment, the polypeptide of interest is a growth hormone. The growth hormone may include, but is not limited to, a human growth hormone, a prolactin, a follicle stimulating hormone, a chorionic gonadotrophin, a leuteinizing hormone, a thyroid stimulating hormone, a parathyroid hormone, an estrogen, a progesterone, a testosterone, an insulin, a proinsulin, and any structural or functional analog thereof.

The present invention further relates to the expression of neurotransmitters using the method taught herein. Examples of neurotransmitters include, but are not limited to, an endorphin, a coricotropin releasing hormone, an adrenocorticotropic hormone, a vasopressin, a giractide, an N-acytlaspartylglutamate, a peptide neurotransmitter derived from preopiomelanocortin, any antagonists thereof, and any agonists thereof.

In another embodiment, the polypeptide of interest is a receptor or fusion protein. The receptor or fusion protein may be, but is not limited to, an interleukin-1, an interleukin-12, a tumor necrosis factor, an erythropoeitin, a tissue plasminogen activator, a thrombopoetin, and any structural or functional analog thereof.

Alternatively, recombinant blood proteins may be isolated by the method of the present invention. Such recombinant proteins include, but are not limited to, an erythropoeitin, a thrombopoeitin, a tissue plasminogen activator, a fibrinogen, a hemoglobin, a transferrin, an albumin, a protein c, and any structural or functional analog thereof.

In another embodiment, the polypeptide of interest is a recombinant antimicrobial agent. Examples of antimicrobial agents contemplated by the present invention include, for example, a beta-lactam, an aminoglycoside, a polypeptide antibiotic, and any structural or functional analog thereof.

The present invention further provides semi-solid capture medium comprising cell growth medium, a gelatinization agent and a capture molecule selected from a receptor or a ligand of or an antibody against the polypeptide of interest. The gelatinization agent may be any polymer that when dissolved in an aqueous cell growth medium, forms semi-solid gel under the temperature suitable for culturing cells. The gelatinization agent may be selected from, but not limited to, agar, agarose, methylcellulose, matrigel, collagen, gelatin, or other similar materials. Preferably, the gelatinization agent is methylcellulose. Such media composition and formulation of the present invention allow the identification of cells expressing the polypeptide of interest by monitoring the precipitate halo formed between the polypeptide of interest and the capture molecule. Accordingly the present invention provides specific media, formulations and methods of making and using thereof.

DESCRIPTION OF THE INVENTION

For many commonly used mammalian expression systems, cloning of stably transfected cells is a time consuming and labor-intensive process. Many hundreds, even thousands of transfected clones are typically screened for high producers because of the random variation in recombinant protein production. The present invention relates to a rapid way to screen for clones producing high levels of polypeptide of interest. The method is based on the precipitates formed between the polypeptide of interest and its corresponding antibody, receptor and/or ligand in a semi-solid capture medium. A halo-like antigen-antibody or receptor-ligand precipitate surrounding the colonies can be observed, the size of which correlates to the level of polypeptide of interest production.

It is well known in the art that if the transfected cells have been in continuous culture for a long time, or the cells in culture are not derived from a single cell clone, they may need to be recloned. The present invention also provides a method to rapidly achieve this goal.

In one embodiment of the present invention, methods are provided for selecting high expression cell clones expressing a polypeptide of interest, comprising: (a) selecting high expression cell clones among cells cultured in a semi-solid culture medium and expressing said polypeptide of interest, wherein said cells are contacted with a capture molecule that interacts with the polypeptide of interest such that said interaction indicates relative expression of said polypeptide for each cell or group of cells. In a preferred embodiment, the semi-solid capture medium is methylcellulose or agar based.

In another embodiment, the present invention provides a method of isolating a polypeptide of interest comprising the steps in addition to above mentioned (a), harvesting and culturing the cell clone; and isolating the polypeptide of interest therefrom.

Polypeptides of Interest

The polypeptides of interest include, but are not limited to, immunoglobulins, integrins, antigens, growth factors, cell cycle proteins, cytokines, hormones, neurotransmitters, receptor or fusion proteins thereof, blood proteins, antimicrobials, or fragments, or structural or functional analogs thereof. These following descriptions do not serve to limit the scope of the invention, but rather illustrate the breadth of the invention.

For example, in one embodiment of the invention, the immunoglobulin may be derived from human or non-human polyclonal or monoclonal antibodies. Specifically, these immunoglobulins (antibodies) may be recombinant and/or synthetic human, primate, rodent, mammalian, chimeric, humanized or CDR-grafted, antibodies and anti-idiotype antibodies thereto. These antibodies can also be produced in a variety of truncated forms in which various portions of antibodies are joined together using genetic engineering techniques. As used presently, an "antibody," "antibody fragment," "antibody variant," "Fab," and the like, include any protein- or peptide-containing molecule that comprises at least a portion of an immunoglobulin molecule, such as but not limited to at least one CDR of a heavy or light chain or a ligand binding portion thereof, a heavy chain or light chain variable region, a heavy chain or light chain constant region, a framework region, or any portion thereof, which may be expressed in the cell culture of the present invention. Such antibodies optionally further affect a specific ligand, such as but not limited to, where such antibody modulates, decreases, increases, antagonizes, agonizes, mitigates, alleviates, blocks, inhibits, abrogates and/or interferes with at least one target activity or binding, or with receptor activity or binding, in vitro, in situ and/or in vivo.

In one embodiment of the invention, such antibodies, or functional equivalents thereof, may be "human," such that they are substantially non-immunogenic in humans. These antibodies may be prepared through any of the methodologies described herein or well know in the art.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof, that are expressed in the cell culture of the present invention. The present invention thus encompasses antibody fragments capable of binding to a biological molecule (such as an antigen or receptor) or portions thereof, including but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments. See, e.g., Current Protocols in Immunology, (Coligan et al., John Wiley & Sons, Inc., NY, N.Y. 1992-2003).

The nature and source of the polypeptide of interest expressed in the cell clones of the present invention are not limited. The following is a general discussion of the variety of proteins, peptides and biological molecules that may be used in the in accordance with the teachings herein. These descriptions do not serve to limit the scope of the invention, but rather illustrate the breadth of the invention.

Thus, an embodiment of the present invention may include the production of one or more growth factors. Briefly, growth factors are hormones or cytokine proteins that bind to receptors on the cell surface, with the primary result of activating cellular proliferation and/or differentiation. Many growth factors are quite versatile, stimulating cellular division in numerous different cell types; while others are specific to a particular cell-type. The following Table 1 presents several factors, but is not intended to be comprehensive or complete, yet introduces some of the more commonly known factors and their principal activities.

TABLE 1

Growth Factors

| Factor | Principal Source | Primary Activity | Comments |
|---|---|---|---|
| Platelet Derived Growth Factor (PDGF) | Platelets, endothelial cells, placenta. | Promotes proliferation of connective tissue, glial and smooth muscle cells. PDGF receptor has intrinsic tyrosine kinase activity. | Dimer required for receptor binding. Two different protein chains, A and B, form 3 distinct dimer forms. |
| Epidermal Growth Factor (EGF) | Submaxillary gland, Brunners gland. | promotes proliferation of mesenchymal, glial and epithelial cells. | EGF receptor has tyrosine kinase activity, activated in response to EGF binding. |
| Fibroblast Growth Factor (FGF) | Wide range of cells; protein is associated with the ECM; nineteen family members. | Promotes proliferation of many cells including skeletal and nervous system; inhibits some stem cells; | Four distinct receptors, all with tyrosine kinase activity. FGF |

TABLE 1-continued

Growth Factors

| Factor | Principal Source | Primary Activity | Comments |
|---|---|---|---|
| | Receptors widely distributed in bone, implicated in several bone-related diseases. | induces mesodermal differentiation. Non-proliferative effects include regulation of pituitary and ovarian cell function. | implicated in mouse mammary tumors and Kaposi's sarcoma. |
| NGF | | Promotes neurite outgrowth and neural cell survival. | Several related proteins first identified as proto-oncogenes; trkA (trackA), trkB, trkC. |
| Erythropoietin (Epo) | Kidney. | Promotes proliferation and differentiation of erythrocytes. | Also considered a 'blood protein,' and a colony stimulating factor. |
| Transforming Growth Factor a (TGF-a) | Common in transformed cells, found in macrophages and keratinocytes. | Potent keratinocyte growth factor. | Related to EGF. |
| Transforming Growth Factor v (TGF-b) | Tumor cells, activated TH$_1$ cells (T-helper) and natural killer (NK) cells. | Anti-inflammatory (suppresses cytokine production and class II MHC expression), proliferative effects on many mesenchymal and epithelial cell types, may inhibit macrophage and lymphocyte proliferation. | Large family of proteins including activin, inhibin and bone morpho-genetic protein. Several classes and subclasses of cell-surface receptors. |
| Insulin-Like Growth Factor-I (IGF-I) | Primarily liver, produced in response to GH and then induces subsequent cellular activities, particularly on bone growth. | Promotes proliferation of many cell types, autocrine and paracrine activities in addition to the initially observed endocrine activities on bone. | Related to IGF-II and proinsulin, also called Somatomedin C. IGF-I receptor, like the insulin receptor, has intrinsic tyrosine kinase activity. IGF-I can bind to the insulin receptor. |
| Insulin-Like Growth Factor-II (IGF-II) | Expressed almost exclusively in embryonic and neonatal tissues. | Promotes proliferation of many cell types primarily of fetal origin. Related to IGF-I and proinsulin. | IGF-II receptor is identical to the mannose-6-phosphate receptor that is responsible for the integration of lysosomal enzymes. |

Additional growth factors that may be produced in accordance with the present invention include Activin (Vale et al., 321 Nature 776 (1986); Ling et al., 321 Nature 779 (1986)), Inhibin (U.S. Pat. Nos. 4,737,578; 4,740,587), and Bone Morphongenic Proteins (BMPs) (U.S. Pat. No. 5,846,931; Wozney, Cellular & Molecular Biology of Bone 131-167 (1993)).

In addition to the growth factors discussed above, the present invention may target or use other cytokines. Secreted primarily from leukocytes, cytokines stimulate both the humoral and cellular immune responses, as well as the activation of phagocytic cells. Cytokines that are secreted from lymphocytes are termed lymphokines, whereas those secreted by monocytes or macrophages are termed monokines. A large family of cytokines are produced by various cells of the body. Many of the lymphokines are also known as interleukins (ILs), because they are not only secreted by leukocytes, growth factors targeted to cells of hematopoietic origin. The list of identified interleukins grows continuously. See, e.g., U.S. Pat. No. 6,174,995; U.S. Pat. No. 6,143,289; Sallusto et al., 18 Annu. Rev. Immunol. 593 (2000); Kunkel et al., 59 J. Leukocyto Biol. 81 (1996).

Additional growth factor/cytokines encompassed in the present invention include pituitary hormones such as human growth hormone (HGH), follicle stimulating hormones (FSH, FSHα, and FSHβ), Human Chorionic Gonadotrophins (HCG, HCGα, HCGβ), uFSH (urofollitropin), Gonatropin releasing hormone (GRH), Growth Hormone (GH), leuteinizing hormones (LH, LHα, LHβ), somatostatin, prolactin, thyrotropin (TSH, TSHα, TSHβ), thyrotropin releasing hormone (TRH), parathyroid hormones, estrogens, progesterones, testosterones, or structural or functional analog thereof. All of these proteins and peptides are known in the art.

The cytokine family also includes tumor necrosis factors, colony stimulating factors, and interferons. See, e.g., Cosman, 7 Blood Cell (1996); Gruss et al., 85 Blood 3378 (1995); Beutler et al., 7 Annu. Rev. Immunol. 625 (1989); Aggarwal et al., 260 J. Biol. Chem. 2345 (1985); Pennica et al., 312 Nature 724 (1984); R & D Systems, Cytokine Mini-Reviews, at http://www.rndsystems.com.

Several cytokines are introduced, briefly, in Table 2 below.

TABLE 2

Cytokines

| Cytokine | Principal Source | Primary Activity |
| --- | --- | --- |
| Interleukins IL1-a and -b | Primarily macrophages but also neutrophils, endothelial cells, smooth muscle cells, glial cells, astrocytes, B- and T-cells, fibroblasts, and keratinocytes | Costimulation of APCs and T cells; stimulates IL-2 receptor production and expression of interferon-γ; may induce proliferation in non-lymphoid cells. |
| IL-2 | CD4+ T-helper cells, activated $TH_1$ cells, NK cells | Major interleukin responsible for clonal T-cell proliferation. IL-2 also exerts effects on B-cells, macrophages, and natural killer (NK) cells. IL-2 receptor is not expressed on the surface of resting T-cells, but expressed constitutively on NK cells, that will secrete TNF-α, IFN-γ and GM-CSF in response to IL-2, which in turn activate macrophages. |
| IL-3 | Primarily T-cells | Also known as multi-CSF, as it stimulates stem cells to produce all forms of hematopoietic cells. |
| IL-4 | $TH_2$ and mast cells | B cell proliferation, eosinophil and mast cell growth and function, IgE and class II MHC expression on B cells, inhibition of monokine production |
| IL-5 | $TH_2$ and mast cells | eosinophil growth and function |
| IL-6 | Macrophages, fibroblasts, endothelial cells and activated T-helper cells. Does not induce cytokine expression. | IL-6 acts in synergy with IL-1 and TNF-α in many immune responses, including T-cell activation; primary inducer of the acute-phase response in liver; enhances the differentiation of B-cells and their consequent production of immunoglobulin; enhances Glucocorticoid synthesis. |
| IL-7 | thymic and marrow stromal cells | T and B lymphopoiesis |
| IL-8 | Monocytes, neutrophils, macrophages, and NK cells | Chemoattractant (chemokine) for neutrophils, basophils and T-cells; activates neutrophils to degranulate. |
| IL-9 | T cells | hematopoietic and thymopoietic effects |
| IL-10 | activated $TH_2$ cells, $CD8^+$ T and B cells, macrophages | inhibits cytokine production, promotes B cell proliferation and antibody production, suppresses cellular immunity, mast cell growth |
| IL-11 | stromal cells | synergisitc hematopoietic and thrombopoietic effects |
| IL-12 | B cells, macrophages | proliferation of NK cells, INF-g production, promotes cell-mediated immune functions |
| IL-13 | $TH_2$ cells | IL-4-like activities |
| IL-18 | macrophages/Kupffer cells, keratinocytes, glucocorticoid-secreting adrenal cortex cells, and osteoblasts | Interferon-gamma-inducing factor with potent pro-inflammatory activity |
| IL-21 | Activated T cells | IL21 has a role in proliferation and maturation of natural killer (NK) cell populations from bone marrow, in the proliferation of mature B-cell populations co-stimulated with anti-CD40, and in the proliferation of T cells co-stimulated with anti-CD3. |
| IL-23 | Activated dendritic cells | A complex of p19 and the p40 subunit of IL-12. IL-23 binds to IL-12R beta 1 but not IL-12R beta 2; activates Stat4 in PHA blast T cells; induces strong proliferation of mouse memory T cells; stimulates IFN-gamma production and proliferation in PHA blast T cells, as well as in CD45RO (memory) T cells. |
| TumorNecrosis Factor TNF-α | Primarily activated macrophages. | Once called cachectin; induces the expression of other autocrine growth factors, increases cellular responsiveness to growth factors; induces signaling pathways that lead to proliferation; induces expression of a number of nuclear proto-oncogenes as well as of several interleukins. |

TABLE 2-continued

Cytokines

| Cytokine | Principal Source | Primary Activity |
|---|---|---|
| (TNF-β) | T-lymphocytes, particularly cytotoxic T-lymphocytes (CTL cells); induced by IL-2 and antigen-T-Cell receptor interactions. | Also called lymphotoxin; kills a number of different cell types, induces terminal differentiation in others; inhibits lipoprotein lipase present on the surface of vascular endothelial cells. |
| Interferons INF-a and -b | macrophages, neutrophils and some somatic cells | Known as type I interferons; antiviral effect; induction of class I MHC on all somatic cells; activation of NK cells and macrophages. |
| Interferon INF-γ | Primarily CD8+ T-cells, activated $TH_1$ and NK cells | Type II interferon; induces of class I MHC on all somatic cells, induces class II MHC on APCs and somatic cells, activates macrophages, neutrophils, NK cells, promotes cell-mediated immunity, enhances ability of cells to present antigens to T-cells; antiviral effects. |
| Monocyte Chemoattractant Protein-1 (MCP1) | Peripheral blood monocytes/macrophages | Attracts monocytes to sites of vascular endothelial cell injury, implicated in atherosclerosis. |
| Colony Stimulating Factors (CSFs) | | Stimulate the proliferation of specific pluripotent stem cells of the bone marrow in adults. |
| Granulocyte-CSF (G-CSF) | | Specific for proliferative effects on cells of the granulocyte lineage; proliferative effects on both classes of lymphoid cells. |
| Macrophage-CSF (M-CSF) | | Specific for cells of the macrophage lineage. |
| Granulocyte-MacrophageCSF (GM-CSF) | | Proliferative effects on cells of both the macrophage and granulocyte lineages. |

Other cytokines of interest that may be produced by the invention described herein include adhesion molecules (R & D Systems, Adhesion Molecule (1996), at http://www.rnd-systems.com); angiogenin (U.S. Pat. No. 4,721,672; Moener et al., 226 Eur. J. Biochem. 483 (1994)); annexin V (Cookson et al., 20 Genomics 463 (1994); Grundmann et al., 85 Proc. Natl. Acad. Sci. USA 3708 (1988); U.S. Pat. No. 5,767,247); caspases (U.S. Pat. No. 6,214,858; Thornberry et al., 281 Science 1312 (1998)); chemokines (U.S. Pat. Nos. 6,174,995; 6,143,289; Sallusto et al., 18 Annu. Rev. Immunol. 593 (2000) Kunkel et al., 59 J. Leukocyte Biol. 81 (1996)); endothelin (U.S. Pat. Nos. 6,242,485; 5,294,569; 5,231,166); eotaxin (U.S. Pat. No. 6,271,347; Ponath et al., 97(3) J. Clin. Invest. 604-612 (1996)); Flt-3 (U.S. Pat. No. 6,190,655); heregulins (U.S. Pat. Nos. 6,284,535; 6,143,740; 6,136,558; 5,859,206; 5,840,525); Leptin (Leroy et al., 271(5) J. Biol. Chem. 2365 (1996); Maffei et al., 92 Proc. Natl. Acad. Sci. USA 6957 (1995); Zhang Y. et al. (1994) Nature 372: 425-432); Macrophage Stimulating Protein (MSP) (U.S. Pat. Nos. 6,248,560; 6,030,949; 5,315,000); Neurotrophic Factors (U.S. Pat. Nos. 6,005,081; 5,288,622); Pleiotrophin/Midkine (PTN/MK) (Pedraza et al., 117 J. Biochem. 845 (1995); Tamura et al., 3 Endocrine 21 (1995); U.S. Pat. No. 5,210,026; Kadomatsu et al., 151 Biochem. Biophys. Res. Commun. 1312 (1988)); STAT proteins (U.S. Pat. Nos. 6,030,808; 6,030,780; Darnell et al., 277 Science 1630-1635 (1997)); Tumor Necrosis Factor Family (Cosman, 7 Blood Cell (1996); Gruss et al., 85 Blood 3378 (1995); Beutler et al., 7 Annu. Rev. Immunol. 625 (1989); Aggarwal et al., 260 J. Biol. Chem. 2345 (1985); Pennica et al., 312 Nature 724 (1984)).

The present invention may also be used to affect blood proteins, a generic name for a vast group of proteins generally circulating in blood plasma, and important for regulating coagulation and clot dissolution. See, e.g., Haematologic Technologies, Inc., HTI Catalog, at www.haemtech.com. Table 3 introduces, in a non-limiting fashion, some of the blood proteins contemplated by the present invention.

TABLE 3

Blood Proteins

| Protein | Principle Activity | Reference |
|---|---|---|
| Factor V | In coagulation, this glycoprotein pro-cofactor, is converted to active cofactor, factor Va, via the serine protease α-thrombin, and less efficiently by its serine protease cofactor Xa. The prothrombinase complex rapidly converts zymogen prothrombin to the active serine | Mann et al., 57 ANN. REV. BIOCHEM. 915 (1988); see also Nesheim et al., 254 J. BIOL. CHEM. 508 (1979); Tracy et al., 60 BLOOD 59 (1982); Nesheim et al., 80 METHODS ENZYMOL. 249 (1981); Jenny et al., 84 PROC. NATL. ACAD. SCI. USA 4846 (1987). |

TABLE 3-continued

Blood Proteins

| Protein | Principle Activity | Reference |
| --- | --- | --- |
| | protease, α-thrombin. Down regulation of prothrombinase complex occurs via inactivation of Va by activated protein C. | |
| Factor VII | Single chain glycoprotein zymogen in its native form. Proteolytic activation yields enzyme factor VIIa, which binds to integral membrane protein tissue factor, forming an enzyme complex that proteolytically converts factor X to Xa. Also known as extrinsic factor Xase complex. Conversion of VII to VIIa catalyzed by a number of proteases including thrombin, factors IXa, Xa, XIa, and XIIa. Rapid activation also occurs when VII combines with tissue factor in the presence of Ca, likely initiated by a small amount of pre-existing VIIa. Not readily inhibited by antithrombin III/heparin alone, but is inhibited when tissue factor added. | See generally, Broze et al., 80 METHODS ENZYMOL. 228 (1981); Bajaj et al., 256 J. BIOL. CHEM. 253 (1981); Williams et al., 264 J. BIOL. CHEM. 7536 (1989); Kisiel et al., 22 THROMBOSIS RES. 375 (1981); Seligsohn et al., 64 J. CLIN. INVEST. 1056 (1979); Lawson et al., 268 J. BIOL. CHEM. 767 (1993). |
| Factor IX | Zymogen factor IX, a single chain vitamin K-dependent glycoprotein, made in liver. Binds to negatively charged phospholipid surfaces. Activated by factor XIα or the factor VIIa/tissue factor/phospholipid complex. Cleavage at one site yields the intermediate IXα, subsequently converted to fully active form IXαβ by cleavage at another site. Factor IXαβ is the catalytic component of the "intrinsic factor Xase complex" (factor VIIIa/IXa/Ca$^{2+}$/phospholipid) that proteolytically activates factor X to factor Xa. | Thompson, 67 BLOOD, 565 (1986); Hedner et al., HEMOSTASIS AND THROMBOSIS 39-47 (R. W. Colman, J. Hirsh, V. J. Marder, E. W. Salzman ed., 2$^{nd}$ ed. J. P. Lippincott Co., Philadelphia) 1987; Fujikawa et al., 45 METHODS IN ENZYMOLOGY 74 (1974). |
| Factor X | Vitamin K-dependent protein zymogen, made in liver, circulates in plasma as a two chain molecule linked by a disulfide bond. Factor Xa (activated X) serves as the enzyme component of prothrombinase complex, responsible for rapid conversion of prothrombin to thrombin. | See Davie et al., 48 ADV. ENZYMOL 277 (1979); Jackson, 49 ANN. REV. BIOCHEM. 765 (1980); see also Fujikawa et al., 11 BIOCHEM. 4882 (1972); Discipio et al., 16 BIOCHEM. 698 (1977); Discipio et al., 18 BIOCHEM. 899 (1979); Jackson et al., 7 BIOCHEM. 4506 (1968); McMullen et al., 22 BIOCHEM. 2875 (1983). |
| Factor XI | Liver-made glycoprotein homodimer circulates, in a non-covalent complex with high molecular weight kininogen, as a zymogen, requiring proteolytic activation to acquire serine protease activity. Conversion of factor XI to factor XIa is catalyzed by factor XIIa. XIa unique among the serine proteases, since it contains two active sites per molecule. Works in the intrinsic coagulation pathway by catalyzing conversion of factor IX to factor IXa. Complex form, factor XIa/HMWK, activates factor XII to factor XIIa and prekallikrein to kallikrein. Major inhibitor of XIa is a$_1$-antitrypsin and to lesser extent, antithrombin-III. Lack of factor XI procoagulant activity causes bleeding disorder: plasma thromboplastin antecedent deficiency. | Thompson et al., 60 J. CLIN. INVEST. 1376 (1977); Kurachi et al., 16 BIOCHEM. 5831 (1977); Bouma et al., 252 J. BIOL. CHEM. 6432 (1977); Wuepper, 31 FED. PROC. 624 (1972); Saito et al., 50 BLOOD 377 (1977); Fujikawa et al., 25 BIOCHEM. 2417 (1986); Kurachi et al., 19 BIOCHEM. 1330 (1980); Scott et al., 69 J. CLIN. INVEST. 844 (1982). |
| Factor XII (Hageman Factor) | Glycoprotein zymogen. Reciprocal activation of XII to active serine protease factor XIIa by kallikrein is central to start of intrinsic coagulation pathway. Surface bound α-XIIa activates factor XI to XIa. Secondary cleavage of α-XIIa by kallikrein yields β-XIIa, and catalyzes solution phase activation of | Schmaier et al., 18-38, and Davie, 242-267 HEMOSTASIS & THROMBOSIS (Colman et al., eds., J. B. Lippincott Co., Philadelphia, 1987). |

TABLE 3-continued

Blood Proteins

| Protein | Principle Activity | Reference |
|---|---|---|
| | kallikrein, factor VII and the classical complement cascade. | |
| Factor XIII | Zymogenic form of glutaminyl-peptide γ-glutamyl transferase factor XIIIa (fibrinoligase, plasma transglutaminase, fibrin stabilizing factor). Made in the liver, found extracellularly in plasma and intracellularly in platelets, megakaryocytes, monocytes, placenta, uterus, liver and prostrate tissues. Circulates as a tetramer of 2 pairs of nonidentical subunits ($A_2B_2$). Full expression of activity is achieved only after the $Ca^{2+}$ - and fibrin(ogen)- dependent dissociation of B subunit dimer from $A_2$' dimer. Last of the zymogens to become activated in the coagulation cascade, the only enzyme in this system that is not a serine protease. XIIIa stabilizes the fibrin clot by crosslinking the α and γ-chains of fibrin. Serves in cell proliferation in wound healing, tissue remodeling, atherosclerosis, and tumor growth. | See McDonaugh, 340-357 HEMOSTASIS & THROMBOSIS (Colman et al., eds., J. B. Lippincott Co., Philadelphia, 1987); Folk et al., 113 METHODS ENZYMOL. 364 (1985); Greenberg et al., 69 BLOOD 867 (1987). Other proteins known to be substrates for Factor XIIIa, that may be hemostatically important, include fibronectin (Iwanaga et al., 312 ANN. NY ACAD. SCI. 56 (1978)), $a_2$-antiplasmin (Sakata et al., 65 J. CLIN. INVEST. 290 (1980)), collagen (Mosher et al., 64 J. CLIN. INVEST. 781 (1979)), factor V (Francis et al., 261 J. BIOL. CHEM. 9787 (1986)), von Willebrand Factor (Mosher et al., 64 J. CLIN. INVEST. 781 (1979)) and thrombospondin (Bale et al., 260 J. BIOL. CHEM. 7502 (1985); Bohn, 20 MOL. CELL BIOCHEM. 67 (1978)). |
| Fibrinogen | Plasma fibrinogen, a large glycoprotein, disulfide linked dimer made of 3 pairs of non-identical chains (Aa, Bb and g), made in liver. Aa has N-terminal peptide (fibrinopeptide A (FPA), factor XIIIa crosslinking sites, and 2 phosphorylation sites. Bb has fibrinopeptide B (FPB), 1 of 3 N-linked carbohydrate moieties, and an N-terminal pyroglutamic acid. The g chain contains the other N-linked glycos. site, and factor XIIIa cross-linking sites. Two elongated subunits $((AaBbg)_2)$ align in an antiparallel way forming a trinodular arrangement of the 6 chains. Nodes formed by disulfide rings between the 3 parallel chains. Central node (n-disulfide knot, E domain) formed by N-termini of all 6 chains held together by 11 disulfide bonds, contains the 2 IIa-sensitive sites. Release of FPA by cleavage generates Fbn I, exposing a polymerization site on Aa chain. These sites bind to regions on the D domain of Fbn to form proto-fibrils. Subsequent IIa cleavage of FPB from the Bb chain exposes additional polymerization sites, promoting lateral growth of Fbn network. Each of the 2 domains between the central node and the C-terminal nodes (domains D and E) has parallel ahelical regions of the Aa, Bb and g chains having protease- (plasmin-) sensitive sites. Another major plasmin sensitive site is in hydrophilic preturbance of a-chain from C-terminal node. Controlled plasmin degradation converts Fbg into fragments D and E. | FURLAN, Fibrinogen, IN HUMAN PROTEIN DATA, (Haeberli, ed., VCH Publishers, N.Y.,1995); Doolittle, in HAEMOSTASIS & THROMBOSIS, 491-513 (3rd ed., Bloom et al., eds., Churchill Livingstone, 1994); HANTGAN, et al., in HAEMOSTASIS & THROMBOSIS 269-89 (2d ed., Forbes et al., eds., Churchill Livingstone, 1991). |
| Fibronectin | High molecular weight, adhesive, glycoprotein found in plasma and extracellular matrix in slightly different forms. Two peptide chains interconnected by 2 disulfide bonds, has 3 different types of repeating homologous sequence units. | Skorstengaard et al., 161 Eur. J. BIOCHEM. 441 (1986); Kornblihtt et al., 4 EMBO J. 1755 (1985); Odermatt et al., 82 PNAS 6571 (1985); Hynes, R.O., ANN. REV. CELL BIOL., 1, 67 (1985); Mosher 35 ANN. REV. MED. 561 (1984); |

TABLE 3-continued

Blood Proteins

| Protein | Principle Activity | Reference |
|---|---|---|
| | Mediates cell attachment by interacting with cell surface receptors and extracellular matrix components. Contains an Arg-Gly-Asp-Ser (RGDS) cell attachment-promoting sequence, recognized by specific cell receptors, such as those on platelets. Fibrin-fibronectin complexes stabilized by factor XIIIa-catalyzed covalent cross-linking of fibronectin to the fibrin a chain. | Rouslahti et al., 44 Cell 517 (1986); Hynes 48 CELL 549 (1987); Mosher 250 BIOL. CHEM. 6614 (1975). |
| $b_2$-Glycoprotein I | Also called $b_2$I and Apolipoprotein H. Highly glycosylated single chain protein made in liver. Five repeating mutually homologous domains consisting of approximately 60 amino acids disulfide bonded to form Short Consensus Repeats (SCR) or Sushi domains. Associated with lipoproteins, binds anionic surfaces like anionic vesicles, platelets, DNA, mitochondria, and heparin. Binding can inhibit contact activation pathway in blood coagulation. Binding to activated platelets inhibits platelet associated prothrombinase and adenylate cyclase activities. Complexes between $b_2$I and cardiolipin have been implicated in the anti-phospholipid related immune disorders LAC and SLE. | See, e.g., Lozier et al., 81 PNAS 2640-44 (1984); Kato & Enjyoi 30 BIOCHEM. 11687-94 (1997); Wurm, 16 INT'L J. BIOCHEM. 511-15 (1984); Bendixen et al., 31 BIOCHEM. 3611-17 (1992); Steinkasserer et al., 277 BIOCHEM. J. 387-91 (1991); Nimpf et al., 884 BIOCHEM. BIOPHYS. ACTA 142-49 (1986); Kroll et.al. 434 BIOCHEM. BIOPHYS. Acta 490-501 (1986); Polz et al., 11 INT'L J. BIOCHEM. 265-73 (1976); McNeil et al., 87 PNAS 4120-24 (1990); Galli et al;. I LANCET 1544-47 (1990); Matsuuna et al., II LANCET 177-78 (1990); Pengo et al., 73 THROMBOSIS & HAEMOSTASIS 29-34 (1995). |
| Osteonectin | Acidic, noncollagenous glycoprotein (Mr = 29,000) originally isolated from fetal and adult bovine bone matrix. May regulate bone metabolism by binding hydroxyapatite to collagen. Identical to human placental SPARC. An alpha granule component of human platelets secreted during activation. A small portion of secreted osteonectin expressed on the platelet cell surface in an activation-dependent manner | Villarreal et al., 28 BIOCHEM. 6483 (1989); Tracy et al., 29 INT'L J. BIOCHEM. 653 (1988); Romberg et al., 25 BIOCHEM. 1176 (1986); Sage & Bornstein 266 J. BIOL. CHEM. 14831 (1991); Kelm & Mann 4 J. BONE MIN. RES. 5245 (1989); Kelm et al., 80 BLOOD 3112 (1992). |
| Plasminogen | Single chain glycoprotein zymogen with 24 disulfide bridges, no free sulfhydryls, and 5 regions of internal sequence homology, "kringles", each five triple-looped, three disulfide bridged, and homologous to kringle domains in t-PA, u-PA and prothrombin. Interaction of plasminogen with fibrin and α2-antiplasmin is mediated by lysine binding sites. Conversion of plasminogen to plasmin occurs by variety of mechanisms, including urinary type and tissue type plasminogen activators, streptokinase, staphylokinase, kallikrein, factors IXa and XIIa, but all result in hydrolysis at Arg560-Val561, yielding two chains that remain covalently associated by a disulfide bond. | See Robbins, 45 METHODS IN ENZYMOLOGY 257 (1976); COLLEN, 243-258 BLOOD COAG. (Zwaal et al., eds., New York, Elsevier, 1986); see also Castellino et al., 80 METHODS IN ENZYMOLOGY 365 (1981); Wohl et al., 27 THROMB. RES. 523 (1982); Barlow et al., 23 BIOCHEM. 2384 (1984); SOTTRUP-JENSEN ET AL., 3 PROGRESS IN CHEM. FIBRINOLYSIS & THROMBOLYSIS 197-228 (Davidson et al., eds., Raven Press, New York 1975). |
| tissue Plasminogen Activator | t-PA, a serine endopeptidase synthesized by endothelial cells, is the major physiologic activator of plasminogen in clots, catalyzing conversion of plasminogen to plasmin by hydrolising a specific arginine-alanine bond. Requires fibrin for this activity, unlike the kidney-produced version, urokinase-PA. | See Plasminogen. |
| Plasmin | See Plasminogen. Plasmin, a serine protease, cleaves fibrin, and activates | See Plasminogen. |

TABLE 3-continued

Blood Proteins

| Protein | Principle Activity | Reference |
|---|---|---|
| | and/or degrades compounds of coagulation, kinin generation, and complement systems. Inhibited by a number of plasma protease inhibitors in vitro. Regulation of plasmin in vivo occurs mainly through interaction with $a_2$-antiplasmin, and to a lesser extent, $a_2$-macroglobulin. | |
| Platelet Factor-4 | Low molecular weight, heparin-binding protein secreted from agonist-activated platelets as a homotetramer in complex with a high molecular weight, proteoglycan, carrier protein. Lysine-rich, COOH-terminal region interacts with cell surface expressed heparin-like glycosaminoglycans on endothelial cells, PF-4 neutralizes anticoagulant activity of heparin exerts procoagulant effect, and stimulates release of histamine from basophils. Chemotactic activity toward neutrophils and monocytes. Binding sites on the platelet surface have been identified and may be important for platelet aggregation. | Rucinski et al., 53 BLOOD 47 (1979); Kaplan et al., 53 BLOOD 604 (1979); George 76 BLOOD 859 (1990); Busch et al., 19 THROMB. RES. 129 (1980); Rao et al., 61 BLOOD 1208 (1983); Brindley, et al., 72 J. CLIN. INVEST. 1218 (1983); Deuel et al., 74 PNAS 2256 (1981); Osterman et al., 107 BIOCHEM. BIOPHYS. RES. COMMUN. 130 (1982); Capitanio et al., 839 BIOCHEM. BIOPHYS. ACTA 161 (1985). |
| Protein C | Vitamin K-dependent zymogen, protein C, made in liver as a single chain polypeptide then converted to a disulfide linked heterodimer. Cleaving the heavy chain of human protein C converts the zymogen into the serine protease, activated protein C. Cleavage catalyzed by a complex of α-thrombin and thrombomodulin. Unlike other vitamin K dependent coagulation factors, activated protein C is an anticoagulant that catalyzes the proteolytic inactivation of factors Va and VIIIa, and contributes to the fibrinolytic response by complex formation with plasminogen activator inhibitors. | See Esmon, 10 PROGRESS IN THROMB. & HEMOSTS. 25 (1984); Stenflo, 10 SEMIN. IN THROMB. & HEMOSTAS. 109 (1984); Griffen et al., 60 BLOOD 261 (1982); Kisiel et al., 80 METHODS ENZYMOL. 320 (1981); Discipio et al., 18 BIOCHEM. 899 (1979). |
| Protein S | Single chain vitamin K-dependent protein functions in coagulation and complement cascades. Does not possess the catalytic triad. Complexes to C4b binding protein (C4BP) and to negatively charged phospholipids, concentrating C4BP at cell surfaces following injury. Unbound S serves as anticoagulant cofactor protein with activated Protein C. A single cleavage by thrombin abolishes protein S cofactor activity by removing gla domain. | Walker 10 SEMIN. THROMB. HEMOSTAS. 131 (1984); Dahlback et al., 10 SEMIN. THROMB. HEMOSTAS., 139 (1984); Walker 261 J. BIOL. CHEM. 10941 (1986). |
| Protein Z | Vitamin K-dependent, single-chain protein made in the liver. Direct requirement for the binding of thrombin to endothelial phospholipids. Domain structure similar to that of other vitamin K-dependant zymogens like factors VII, IX, X, and protein C. N-terminal region contains carboxyglutamic acid domain enabling phospholipid membrane binding. C-terminal region lacks "typical" serine protease activation site. Cofactor for inhibition of coagulation factor Xa by serpin called protein Z-dependant protease inhibitor. Patients diagnosed with protein Z deficiency have abnormal bleeding diathesis during and after surgical events. | Sejima et al., 171 BIOCHEM. BIOPHYSICS RES. COMM. 661 (1990); Hogg et al., 266 J. BIOL. CHEM. 10953 (1991); Hogg et al., 17 BIOCHEM. BIOPHYSICS RES. COMM. 801 (1991); Han et al., 38 BIOCHEM. 11073 (1999); Kemkes-Matthes et al., 79 THROMB. RES. 49 (1995). |

TABLE 3-continued

Blood Proteins

| Protein | Principle Activity | Reference |
| --- | --- | --- |
| Prothrombin | Vitamin K-dependent, single-chain protein made in the liver. Binds to negatively charged phospholipid membranes. Contains two "kringle" structures. Mature protein circulates in plasma as a zymogen and, during coagulation, is proteolytically activated to the potent serine protease α-thrombin. | Mann et al., 45 METHODS IN ENZYMOLOGY 156 (1976); Magnusson et al., PROTEASES IN BIOLOGICAL CONTROL 123-149 (Reich et al., eds. Cold Spring Harbor Labs., New York 1975); Discipio et al., 18 BIOCHEM. 899 (1979). |
| α-Thrombin | See Prothrombin. During coagulation, thrombin cleaves fibrinogen to form fibrin, the terminal proteolytic step in coagulation, forming the fibrin clot. Thrombin also responsible for feedback activation of procofactors V and VIII. Activates factor XIII and platelets, functions as vasoconstrictor protein. Procoagulant activity arrested by heparin cofactor II or the antithrombin III/heparin complex, or complex formation with thrombomodulin. Formation of thrombin/thrombomodulin complex results in inability of thrombin to cleave fibrinogen and activate factors V and VIII, but increases the efficiency of thrombin for activation of the anticoagulant, protein C. | 45 METHODS ENZYMOL. 156 (1976). |
| b-Thromboglobulin | Low molecular weight, heparin-binding, platelet-derived tetramer protein, consisting of four identical peptide chains. Lower affinity for heparin than PF-4. Chemotactic activity for human fibroblasts, other functions unknown. | See, e.g., George 76 BLOOD 859 (1990); Holt & Niewiarowski 632 BIOCHIM. BIOPHYS. ACTA 284 (1980); Niewiarowski et al., 55 BLOOD 453 (1980); Varma et al., 701 BIOCHIM. BIOPHYS. ACTA 7 (1982); Senior et al., 96 J. CELL. BIOL. 382 (1983). |
| Thrombopoietin | Human TPO (Thrombopoietin, Mpl-ligand, MGDF) stimulates the proliferation and maturation of megakaryocytes and promotes increased circulating levels of platelets in vivo. Binds to c-Mpl receptor. | Horikawa et al., 90(10) BLOOD 4031-38 (1997); de Sauvage et al., 369 NATURE 533-58 (1995). |
| Thrombospondin | High-molecular weight, heparin-binding glycoprotein constituent of platelets, consisting of three, identical, disulfide-linked polypeptide chains. Binds to surface of resting and activated platelets, may effect platelet adherence and aggregation. An integral component of basement membrane in different tissues. Interacts with a variety of extracellular macromolecules including heparin, collagen, fibrinogen and fibronectin, plasminogen, plasminogen activator, and osteonectin. May modulate cell-matrix interactions. | Dawes et al., 29 THROMB. RES. 569 (1983); Switalska et al., 106 J. LAB. CLIN. MED. 690 (1985); Lawler et al. 260 J. BIOL. CHEM. 3762 (1985); Wolff et al., 261 J. BIOL. CHEM. 6840 (1986); Asch et al., 79 J. CLIN. CHEM. 1054 (1987); Jaffe et al., 295 NATURE 246 (1982); Wright et al., 33 J. HISTOCHEM. CYTOCHEM. 295 (1985); Dixit et al., 259 J. BIOL. CHEM. 10100 (1984); Mumby et al., 98 J. CELL. BIOL. 646 (1984); Lahav et al, 145 EUR. J. BIOCHEM. 151 (1984); Silverstein et al, 260 J. BIOL. CHEM. 10346 (1985); Clezardin et al. 175 EUR. J. BIOCHEM. 275 (1988); Sage & Bornstein (1991). |
| Von Willebrand Factor | Multimeric plasma glycoprotein made of identical subunits held together by disulfide bonds. During normal hemostasis, larger multimers of vWF cause platelet plug formation by forming a bridge between platelet glycoprotein IB and exposed collagen in the subendothelium. Also binds and transports factor VIII (antihemophilic factor) in plasma. | Hoyer 58 BLOOD 1 (1981); Ruggeri & Zimmerman 65 J. CLIN. INVEST. 1318 (1980); Hoyer & Shainoff 55 BLOOD 1056 (1980); Meyer et al., 95 J. LAB. CLIN. INVEST. 590 (1980); Santoro 21 THROMB. RES. 689 (1981); Santoro, & Cowan 2 COLLAGEN RELAT. RES. 31 (1982); Morton et al., 32 THROMB. RES. 545 (1983); Tuddenham et al., 52 BRIT. J. HAEMATOL. 259 (1982). |

Additional blood proteins contemplated herein include the following human serum proteins, which may also be placed in another category of protein (such as hormone or antigen): Actin, Actinin, Amyloid Serum P, Apolipoprotein E, B2-Microglobulin, C-Reactive Protein (CRP), Cholesterylester transfer protein (CETP), Complement C3B, Ceruplasmin, Creatine Kinase, Cystatin, Cytokeratin 8, Cytokeratin 14, Cytokeratin 18, Cytokeratin 19, Cytokeratin 20, Desmin, Desmocollin 3, FAS (CD95), Fatty Acid Binding Protein, Ferritin, Filamin, Glial Filament Acidic Protein, Glycogen Phosphorylase Isoenzyme BB (GPBB), Haptoglobulin, Human Myoglobin, Myelin Basic Protein, Neurofilament, Placental Lactogen, Human SHBG, Human Thyroid Peroxidase, Receptor Associated Protein, Human Cardiac Troponin C, Human Cardiac Troponin 1, Human Cardiac Troponin T, Human Skeletal Troponin I, Human Skeletal Troponin T, Vimentin, Vinculin, Transferrin Receptor, Prealbumin, Albumin, Alpha-1-Acid Glycoprotein, Alpha-1-Antichymotrypsin, Alpha-1-Antitrypsin, Alpha-Fetoprotein, Alpha-1-Microglobulin, Beta-2-microglobulin, C-Reactive Protein, Haptoglobulin, Myoglobulin, Prealbumin, PSA, Prostatic Acid Phosphatase, Retinol Binding Protein, Thyroglobulin, Thyroid Microsomal Antigen, Thyroxine Binding Globulin, Transferrin, Troponin I, Troponin T, Prostatic Acid Phosphatase, Retinol Binding Globulin (RBP). All of these proteins, and sources thereof, are known in the art. Many of these proteins are available commercially from, for example, Research Diagnostics, Inc. (Flanders, N.J.).

The cell clone of the present invention may also express neurotransmitters, or functional portions thereof. Neurotransmitters are chemicals made by neurons and used by them to transmit signals to the other neurons or non-neuronal cells (e.g., skeletal muscle; myocardium, pineal glandular cells) that they innervate. Neurotransmitters produce their effects by being released into synapses when their neuron of origin fires (i.e., becomes depolarized) and then attaching to receptors in the membrane of the post-synaptic cells. This causes changes in the fluxes of particular ions across that membrane, making cells more likely to become depolarized, if the neurotransmitter happens to be excitatory, or less likely if it is inhibitory. Neurotransmitters can also produce their effects by modulating the production of other signal-transducing molecules ("second messengers") in the post-synaptic cells. See, e.g., COOPER, BLOOM & ROTH, THE BIOCHEMICAL BASIS OF NEUROPHARMACOLOGY (7th Ed. Oxford Univ. Press, NYC, 1996); http://web.indstate.edu/theme/mwking/nerves. Neurotransmitters contemplated in the present invention include, but are not limited to, Acetylcholine, Serotonin, γ-aminobutyrate (GABA), Glutamate, Aspartate, Glycine, Histamine, Epinephrine, Norepinephrine, Dopamine, Adenosine, ATP, Nitric oxide, and any of the peptide neurotransmitters such as those derived from pre-opiomelanocortin (POMC), as well as antagonists and agonists of any of the foregoing.

Numerous other proteins or peptides may serve as either targets, or as a source of target-binding moieties as described herein. Table 4 presents a non-limiting list and description of some pharmacologically active peptides that may serve as, or serve as a source of a functional derivative of, the target of the present invention.

TABLE 4

Pharmacologically active peptides

| Binding partner/ Protein of interest (form of peptide) | Pharmacological activity | Reference |
|---|---|---|
| EPO receptor (intrapeptide disulfide-bonded) | EPO mimetic | Wrighton et al., 273 SCIENCE 458-63 (1996); U.S. Pat. No. 5,773,569, issued Jun. 30, 1998. |
| EPO receptor (C-terminally cross-linked dimer) | EPO mimetic | Livnah et al., 273 SCIENCE 464-71 (1996); Wrighton et al., 15 NATURE BIOTECHNOLOGY 1261-5 (1997); Int'l Patent Application WO 96/40772, published Dec. 19, 1996. |
| EPO receptor (linear) | EPO mimetic | Naranda et al., 96 PNAS 7569-74 (1999). |
| c-Mpl (linear) | TPO-mimetic | Cwirla et al., 276 SCIENCE 1696-9 (1997); U.S. Pat. No. 5,869,451, issued Feb. 9, 1999; U.S. Pat. No. 5,932,946, issued Aug. 3, 1999. |
| c-Mpl (C-terminally cross-linked dimer) | TPO-mimetic | Cwirla et al., 276 SCIENCE 1696-9 (1997). |
| (disulfide-linked dimer) | stimulation of hematopoesis ("G-CSF-mimetic") | Paukovits et al., 364 HOPPE-SEYLERS Z. PHYSIOL. CHEM. 30311 (1984); Laerumgal., 16 EXP. HEMAT. 274-80 (1988). |
| (alkylene-linked dimer) | G-CSF-mimetic | Batnagar et al., 39 J. MED. CHEM. 38149 (1996); Cuthbertson et al., 40 J. MED. CHEM. 2876-82 (1997); King et al., 19 EXP. HEMATOL. 481 (1991); King et al., 86(Suppl. 1) BLOOD 309 (1995). |
| IL-1 receptor (linear) | inflammatory and autoimmune diseases ("IL-1 antagonist" or "IL-1 ra-mimetic") | U.S. Pat. No. 5,608,035; U.S. Pat. No. 5,786,331; U.S Pat. No. 5,880,096; Yanofsky et al., 93 PNAS 7381-6 (1996); Akeson et al., 271 J. BIOL. CHEM. 30517-23 (1996); Wiekzorek et al., 49 POL. J. PHARMACOL. 107-17 (1997); Yanofsky, 93 PNAS 7381-7386 (1996). |
| Facteur thyrnique (linear) | stimulation of lymphocytes (FTS-mimetic) | Inagaki-Ohara et al., 171 CELLULAR IMMUNOL. 30-40 (1996); Yoshida, 6 J. IMMUNOPHARMACOL 141-6 (1984). |

TABLE 4-continued

Pharmacologically active peptides

| Binding partner/ Protein of interest (form of peptide) | Pharmacological activity | Reference |
|---|---|---|
| CTLA4 MAb (intrapeptide di-sulfide bonded) | CTLA4-mimetic | Fukumoto et al., 16 NATURE BIOTECH. 267-70 (1998). |
| TNF-a receptor (exo-cyclic) | TNF-a antagonist | Takasaki et al., 15 NATURE BIOTECH. 1266-70 (1997); WO 98/53842, published Dec. 3, 1998. |
| TNF-a receptor (linear) | TNF-a antagonist | Chirinos-Rojas, J. IMM., 5621-26. |
| C3b (intrapeptide di-sulfide bonded) | inhibition of complement activation; autoimmune diseases (C3b antagonist) | Sahu et al., 157 IMMUNOL. 884-91 (1996); Morikis et al., 7 PROTEIN SCI. 619-27 (1998). |
| vinculin (linear) | cell adhesion processes, cell growth, differentiation wound healing, tumor metastasis ("vinculin binding") | Adey et al., 324 BIOCHEM. J. 523-8 (1997). |
| C4 binding protein (C413P) (linear) | anti-thrombotic | Linse et al. 272 BIOL. CHEM. 14658-65 (1997). |
| urokinase receptor (linear) | processes associated with urokinase interaction with its receptor (e.g. angiogenesis, tumor cell invasion and metastasis; (URK antagonist) | Goodson et al., 91 PNAS 7129-33 (1994); International patent application WO 97/35969, published Oct. 2, 1997. |
| Mdm2, Hdm2 (linear) | Inhibition of inactivation of p53 mediated by Mdm2 or hdm2; anti-tumor ("Mdm/hdm antagonist") | Picksley et al., 9 ONCOGENE 2523-9 (1994); Bottger et al. 269 J. MOL. BIOL. 744-56 (1997); Bottger et al., 13 ONCOGENE 13: 2141-7 (1996). |
| $p21^{WAF1}$ (linear) | anti-tumor by mimicking the activity of $p21^{WAF1}$ | Ball et al., 7 CURR. BIOL. 71-80 (1997). |
| farnesyl transferase (linear) | anti-cancer by preventing activation of ras oncogene | Gibbs et al., 77 CELL 175-178 (1994). |
| Ras effector domain (linear) | anti-cancer by inhibiting biological function of the ras oncogene | Moodie et at., 10 TRENDS GENEL 44-48 (1994); Rodriguez et al., 370 NATURE 527-532 (1994). |
| SH2/SH3 domains (linear) | anti-cancer by inhibiting tumor growth with activated tyrosine kinases | Pawson et al, 3 CURR. BIOL. 434-432 (1993); Yu et al., 76 CELL 933-945 (1994). |
| $p16^{INK4}$ (linear) | anti-cancer by mimicking activity of p16; e.g., inhibiting cyclin D-Cdk complex ("p, 16-mimetic") | Fahraeus et al., 6 CURR. BIOL. 84-91 (1996). |
| Src, Lyn (linear) | inhibition of Mast cell activation, IgE-related conditions, type I hypersensitivity ("Mast cell antagonist"). | Stauffer et al., 36 BIOCHEM. 9388-94 (1997). |
| Mast cell protease (linear) | treatment of inflammatory disorders mediated by release of tryptase-6 ("Mast cell protease inhibitors") | International patent application WO 98/33812, published Aug. 6, 1998. |
| SH3 domains (linear) | treatment of SH3-mediated disease states ("SH3 antagonist") | Rickles et al., 13 EMBO J. 5598-5604 (1994); Sparks et al., 269 J. BIOL. CHEM. 238536 (1994); Sparks et al., 93 PNAS 1540-44 (1996). |
| HBV core antigen (HBcAg) (linear) | treatment of HBV viral antigen (HBcAg) infections ("anti-HBV") | Dyson & Muray, PNAS 2194-98 (1995). |
| selectins (linear) | neutrophil adhesion inflammatory diseases ("selectin antagonist") | Martens et al., 270 J. BIOL. CHEM. 21129-36 (1995); European Pat. App. EP 0 714 912, published Jun. 5, 1996. |
| calmodulin (linear, cyclized) | calmodulin antagonist | Pierce et al., 1 MOLEC. DIVEMILY 25965 (1995); Dedman et al., 267 J. BIOL. CHEM. 23025-30 (1993); Adey & Kay, 169 GENE 133-34 (1996). |
| integrins (linear, cyclized) | tumor-homing; treatment for conditions related to integrin-mediated cellular events, including platelet | International patent applications WO 95/14714, published Jun. 1, 1995; WO 97/08203, published Mar. 6, 1997; WO 98/10795, published |

TABLE 4-continued

Pharmacologically active peptides

| Binding partner/ Protein of interest (form of peptide) | Pharmacological activity | Reference |
|---|---|---|
| | aggregation, thrombosis, wound healing, osteoporosis, tissue repair, angiogenesis (e.g., for treatment of cancer) and tumor invasion ("integrin-binding") | Mar. 19, 1998; WO 99/24462, published May 20, 1999; Kraft et al., 274 J. BIOL. CHEM. 1979-85 (1999). |
| fibronectin and extracellular matrix components of T-cells and macrophages (cyclic, linear) | treatment of inflammatory and autoimmune conditions | International patent application WO 98/09985, published Mar. 12, 1998. |
| somatostatin and cortistatin (linear) | treatment or prevention of hormone-producing tumors, acromegaly, giantism, dementia, gastric ulcer, tumor growth, inhibition of hormone secretion, modulation of sleep or neural activity | European patent application EP 0 911 393, published Apr. 28, 1999. |
| bacterial lipopoly-saccharide (linear) | antibiotic; septic shock; disorders modulatable by CAP37 | U.S. Pat. No. 5,877,151, issued Mar. 2, 1999. |
| parclaxin, mellitin (linear or cyclic) | antipathogenic | International patent application WO 97/31019, published Aug. 28 1997. |
| VIP (linear, cyclic) | impotence, neuro-degenerative disorders | International patent application WO 97/40070, published Oct. 30, 1997. |
| CTLs (linear) | cancer | European patent application EP 0 770 624, published May 2, 1997. |
| THF-gamma2 (linear) | | Burnstein, 27 BIOCHEM. 4066-71 (1988). |
| Amylin (linear) | | Cooper, 84 PNAS 8628-32 (1987). |
| Adreno-medullin (linear) | | Kitamura, 192 BBRC 553-60 (1993). |
| VEGF (cyclic, linear) | anti-angiogenic; cancer, rheumatoid arthritis, diabetic retinopathy, psoriasis ("VEGF antagonist") | Fairbrother, 37 BIOCHEM. 17754-64 (1998). |
| MMP (cyclic) | inflammation and autoimmune disorders; tumor growth ("MMP inhibitor") | Koivunen, 17 NATURE BIOTECH. 768-74 (1999). |
| HGH fragment (linear) | | U.S. Pat. No. 5,869,452, issued Feb. 9, 1999. |
| Echistatin | inhibition of platelet aggregation | Gan, 263 J. BIOL. 19827-32 (1988). |
| SLE autoantibody (linear) | SLE | International patent application WO 96/30057, published Oct. 3, 1996. |
| GD1 alpha | suppression of tumor metastasis | Ishikawa et al., 1 FEBS LETT. 20-4 (1998). |
| anti-phospholipid β-2 glycoprotein-1 (β2GPI) antibodies | endothelial cell activation, anti-phospholipid syndrome (APS), thromboembolic phenomena, thrombocytopenia, and recurrent fetal loss | Blank Mal., 96 PNAS 5164-8 (1999). |
| T-Cell Receptor β chain (linear) | diabetes | International patent application WO 96/101214, published Apr. 18, 1996. |
| Binding partner/ Protein of interest (form of peptide) | Pharmacological activity | Reference |
| EPO receptor (intrapeptide disulfide-bonded) | EPO mimetic | Wrighton et al. (1996), Science 273: 458-63; U.S. Pat. No. 5,773,569, issued Jun. 30, 1998 to Wrighton et al. |
| EPO receptor (C-terminally cross-linked dimer) | EPO mimetic | Livnah et al. (1996), Science 273: 464-71; Wrighton et al. (1997), Nature Biotechnology 15: 1261-5; int'l patent application WO 96/40772, published Dec. 19, 1996 |

TABLE 4-continued

Pharmacologically active peptides

| Binding partner/<br>Protein of interest<br>(form of peptide) | Pharmacological activity | Reference |
|---|---|---|
| EPO receptor<br>(linear) | EPO mimetic | Naranda et al., 96 PNAS 7569-74 (1999) |
| c-Mpl<br>(linear) | TPO-mimetic | Cwirla et al.(1997) Science 276: 1696-9; U.S. Pat. No. 5,869,451, issued Feb. 9, 1999; U.S. Pat. No. 5,932,946, issued Aug. 3, 1999 |
| c-Mpl<br>(C-terminally cross-linked dimer) | TPO-mimetic | Cwirla et al. (1997) Science 276: 1696-9 |
| (disulfide-linked dimer) | stimulation of hematopoesis ("G-CSF-mimetic") | Paukovits et al. (1984), Hoppe-Seylers Z. Physiol. Chem. 365: 30311; Laerum gal. (1988), Exp. Hemat. 16: 274-80 |
| (alkylene-linked dimer) | G-CSF-mimetic | Batnagar 91-al. (1996), linked dimer J. Med. Chem. 39: 38149; Cuthbertson et al. (1997), J. Med. Chem. 40: 2876-82; King et al. (1991), Exp. Hematol. 19: 481; King et al. (1995), Blood 86 (Suppl. 1): 309 |
| IL-1 receptor<br>(linear) | inflammatory and autoimmune diseases ("IL-1 antagonist" or "IL-1 ra-mimetic") | U.S. Pat. No. 5,608,035; U.S. Pat. No. 5,786,331; U.S-Pat. No. 5,880,096; Yanofsky 91-al. (1996) PNAS 93: 7381-6; Akeson et al. (1996), J. Biol. Chem. 271: 30517-23; Wiekzorek et al. (1997), Pol. J. Pharmacol. 49: 107-17; Yanofsky (1996), PNAs, 93: 7381-7386. |
| Facteur thyrnique<br>(linear) | stimulation of lymphocytes (FTS-mimetic) | Inagaki-Ohara et al. (1996), Cellular Immunol. 171: 30-40; Yoshida (1984), J. Immunopharmacol, 6: 141-6. |
| CTLA4 MAb<br>(intrapeptide di-sulfide bonded) | CTLA4-mimetic | Fukumoto et al. (1998), Nature Biotech. 16: 267-70 |
| TNF-a receptor<br>(exo-cyclic) | TNF-a antagonist | Takasaki et al. (1997), Nature Biotech. 15: 1266-70; WO 98/53842, published Dec. 3, 1998. |
| TNF-a receptor<br>(linear) | TNF-a antagonist | Chirinos-Rojas J. Imm., 5621-26. |
| C3b<br>(intrapeptide di-sulfide bonded) | inhibition of complement activation; autoimmune diseases (C3b antagonist) | Sahu et al. (1996), Immunol. 157: 884-91; Morikis et al. (1998), Protein Sci. 7: 619-27. |
| vinculin<br>(linear) | cell adhesion processes, cell growth, differentiation wound healing, tumor metastasis ("vinculin binding") | Adey et al. (1997), Biochem. J. 324: 523-8 |
| C4 binding protein (C413P)<br>(linear) | anti-thrombotic | Linse et al. 272 Biol. Chem. 14658-65 (1997) |
| urokinase receptor<br>(linear) | processes associated with urokinase interaction with its receptor (e.g. angiogenesis, tumor cell invasion and metastasis; (URK antagonist) | Goodson et al. (1994), 91 PNAS 7129-33; International application WO 97/35969, published Oct. 2, 1997 |
| Mdm2, Hdm2<br>(linear) | Inhibition of inactivation of p53 mediated by Mdm2 or hdm2; anti-tumor ("Mdm/hdm antagonist") | Picksley et al. (1994), Oncogene 9: 2523-9; Bottger et al. (1997) J. Mol. Biol. 269: 744-56; Bottger et al. (1996), Oncogene 13: 2141-7 |
| p21$^{WAF1}$<br>(linear) | anti-tumor by mimicking the activity of p21$^{WAF1}$ | Ball et al.(1997), Curr. Biol. 7: 71-80. |
| farnesyl transferase<br>(linear) | anti-cancer by preventing activation of ras oncogene | Gibbs et al. (1994), Cell 77: 175-178 |
| Ras effector domain<br>(linear) | anti-cancer by inhibiting biological function of the ras oncogene | Moodie et at. (1994), Trends Genel 10: 44-48 Rodriguez et al. (1994), Nature 370: 527-532. |
| SH2/SH3 domains<br>(linear) | anti-cancer by inhibiting tumor growth with activated tyrosine kinases | Pawson et al (1993), Curr. Biol. 3: 434-432, Yu et al. (1994), Cell 76: 933-945. |
| p16$^{INK4}$<br>(linear) | anti-cancer by mimicking activity of p16; e.g., inhibiting cyclin D-Cdk complex ("p,16-mimetic") | Fahraeus et al. (1996), Curr. Biol. 6: 84-91 |

TABLE 4-continued

Pharmacologically active peptides

| Binding partner/ Protein of interest (form of peptide) | Pharmacological activity | Reference |
|---|---|---|
| Src, Lyn (linear) | inhibition of Mast cell activation, IgE-related conditions, type I hypersensitivity ("Mast cell antagonist"). | Stauffer et al. (1997), Biochem. 36: 9388-94. |
| Mast cell protease (linear) | treatment of inflammatory disorders mediated by release of tryptase-6 ("Mast cell protease inhibitors") | International application WO 98/33812, published Aug. 6, 1998 |
| SH3 domains (linear) | treatment of SH3-mediated disease states ("SH3 antagonist") | Rickles et al. (1994), EMBO J. 13: 5598-5604; Sparks aLal. (1994), J. Biol. Chem. 269: 238536; Sparks et al. (1996), PNAS 93: 1540-44. |
| HBV core antigen (HBcAg) (linear) | treatment of HBV viral antigen (HBcAg) infections ("anti-HBV") | Dyson & Muray (1995), Proc. Natl. Acad. Sci. 92: 2194-98. |
| selectins (linear) | neutrophil adhesion inflammatory diseases ("selectin antagonist") | Martens et al. (1995), J. Biol. Chem. 270: 21129-36; European pat. app. EP 0 714 912, published Jun. 5, 1996 |
| calmodulin (linear, cyclized) | calmodulin antagonist | Pierce et al. (1995), Molec. Divemily 1: 25965; Dedman et al. (1993), J. Biol. Chem. 268: 23025-30; Adey & Kay (1996), Gene 169: 133-34. |
| integrins (linear, cyclized) | tumor-homing; treatment for conditions related to integrin-mediated cellular events, including platelet aggregation, thrombosis, wound healing, osteoporosis, tissue repair, angiogenesis (e.g., for treatment of cancer) and tumor invasion ("integrin-binding") | International applications WO 95/14714, published Jun. 1, 1995; WO 97/08203, published Mar. 6, 1997; WO 98/10795, published Mar. 19, 1998; WO 99/24462, published May 20, 1999; Kraft et al. (1999), J. Biol. Chem. 274: 1979-85. |
| fibronectin and extracellular matrix components of T-cells and macrophages (cyclic, linear) | treatment of inflammatory and autoimmune conditions | WO 98/09985, published Mar. 12, 1998. |
| somatostatin and cortistatin (linear) | treatment or prevention of hormone-producing tumors, acromegaly, giantism, dementia, gastric ulcer, tumor growth, inhibition of hormone secretion, modulation of sleep or neural activity | European patent application 0 911 393, published Apr. 28, 1999. |
| bacterial lipopoly-saccharide (linear) | antibiotic; septic shock; disorders modulatable by CAP37 | U.S. Pat. No. 5,877,151, issued Mar. 2, 1999. |
| parclaxin, mellitin (linear or cyclic) | antipathogenic | WO 97/31019, published 28 Aug. 1997. |
| VIP (linear, cyclic) | impotence, neuro-degenerative disorders | WO 97/40070, published Oct. 30, 1997. |
| CTLs (linear) | cancer | EP 0 770 624, published May 2, 1997. |
| THF-gamma2 (linear) | | Burnstein (1988), Biochem., 27: 4066-71 |
| Amylin (linear) | | Cooper (1987), PNAS 84: 8628-32. |
| Adreno-medullin (linear) | | Kitamura (1993), BBRC, 192: 553-60 |
| VEGF (cyclic, linear) | anti-angiogenic; cancer, rheumatoid arthritis, diabetic retinopathy, psoriasis ("VEGF antagonist'") | Fairbrother (1998), Biochem., 37: 17754-64. |

TABLE 4-continued

Pharmacologically active peptides

| Binding partner/<br>Protein of interest<br>(form of peptide) | Pharmacological activity | Reference |
| --- | --- | --- |
| MMP<br>(cyclic) | inflammation and<br>autoimmune disorders;<br>tumor growth ("MMP<br>inhibitor") | Koivunen 17 Nature Biotech., 768-74<br>(1999). |
| HGH fragment<br>(linear) | | U.S. Pat. No. 5,869,452. |
| Echistatin | inhibition of platelet<br>aggregation | Gan (1988), J. Biol. 263: 19827-32. |
| SLE autoantibody<br>(linear) | SLE | WO 96/30057, published Oct. 3, 1996. |
| GD1 alpha | suppression of tumor<br>metastasis | Ishikawa et al., 1 FEBS Lett. 20-4<br>(1998). |
| anti-phospholipid β-2<br>glycoprotein-1 (β2GPI)<br>antibodies | endothelial cell activation,<br>anti-phospholipid<br>syndrome (APS),<br>thromboembolic<br>phenomena,<br>thrombocytopenia, and<br>recurrent fetal loss | Blank Mal. (1999), PNAS 96: 5164-8. |
| T-Cell Receptor β chain<br>(linear) | diabetes | WO 96/101214, published Apr. 18,<br>1996. |

There are two pivotal cytokines in the pathogenesis of rheumatoid arthritis, IL-1 and TNF-α. They act synergistically to induce each other, other cytokines, and COX-2. Research suggests that IL-1 is a primary mediator of bone and cartilage destruction in rheumatoid arthritis patients, whereas TNF-α appears to be the primary mediator of inflammation.

In a preferred embodiment of the invention, the polypeptide of interest binds to tumor necrosis factor alpha (TNFα), a pro-inflamatory cytokine. U.S. Pat. No. 6,277,969, issued Aug. 21, 2001; U.S. Pat. No. 6,090,382, issued Jul. 10, 2000. Anti-TNFα antibodies have shown great promise as therapeutics. For example, Infliximab, provided commercially as REMICADE® by Centocor, Inc. (Malvern, Pa.) has been used for the treatment of several chronic autoimmune diseases such as Crohn's disease and rheumatoid arthritis. Treacy, 19(4) HUM. EXP. TOXICOL. 226-28 (2000); see also Chantry, 2(1) CURR. OPIN. ANTI-INFLAMMATORY IMMUNOMODULATORY INVEST. DRUGS 31-34 (2000); Rankin et al., 34(4) BRIT. J. RHEUMATOLOGY 334-42 (1995). Preferably, any exposed amino acids of the TNFα-binding moiety of the polypeptide of interest are those with minimal antigenicity in humans, such as human or humanized amino acid sequences. These peptide identities may be generated by screening libraries, as described above, by grafting human amino acid sequences onto murine-derived paratopes (Siegel et al., 7(1) CYTOKINE 15-25 (1995); WO 92/11383, published Jul. 9, 1992) or monkey-derived paratopes (WO 93/02108, published Feb. 4, 1993), or by utilizing xenomice (WO 96/34096, published Oct. 31, 1996). Alternatively, murine-derived anti-TNFα antibodies have exhibited efficacy. Saravolatz et al., 169(1) J. INFECT. DIS. 214-17 (1994).

Alternatively, instead of being derived from an antibody, the TNFα binding moiety of the polypeptide of interest may be derived from the TNFα receptor. For example, Etanercept is a recombinant, soluble TNFα receptor molecule that is administered subcutaneously and binds to TNFα in the patient's serum, rendering it biologically inactive. Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the $C_H2$ domain, the $C_H3$ domain and hinge region, but not the $C_H1$ domain of IgG1. Etanercept is produced by recombinant DNA technology in a Chinese hamster ovary (CHO) mammalian cell expression system. It consists of 934 amino acids and has an apparent molecular weight of approximately 150 kilodaltons. Etanercept may be obtained as ENBREL™, manufactured by Immunex Corp. (Seattle, Wash.). Etanercept may be efficacious in rheumatoid arthritis. Hughes et al., 15(6) BIODRUGS 379-93 (2001).

Another form of human TNF receptor exists as well, identified as p55. Kalinkovich et al., J. INFERON & CYTOKINE RES. 15749-57 (1995). This receptor has also been explored for use in therapy. See, e.g., Qian et al., 118 ARCH. OPHTHALMOL. 1666-71 (2000). A previous formulation of the soluble p55 TNF receptor had been coupled to polyethylene glycol [r-metHuTNFbp PEGylated dimer (TNFbp)], and demonstrated clinical efficacy but was not suitable for a chronic indication due to the development antibodies upon multiple dosing, which resulted in increased clearance of the drug. A second generation molecule was designed to remove the antigenic epitopes of TNFbp, and may be useful in treating patients with rheumatoid arthritis. Davis et al., Presented at the Ann. European Cong. Rheumatology, Nice, France (Jun. 21-24, 2000).

IL-1 receptor antagonist (IL-1Ra) is a naturally occurring cytokine antagonist that demonstrates anti-inflammatory properties by balancing the destructive effects of IL-1α and IL-1β in rheumatoid arthritis but does not induce any intracellular response. Hence, in a preferred embodiment of the invention, the polypeptide of interest comprises IL-1Ra, or any structural or functional analog thereof. Two structural variants of IL-1Ra exist: a 17-kDa form that is secreted from monocytes, macrophages, neutrophils, and other cells (sIL-1Ra) and an 18-kDa form that remains in the cytoplasm of keratinocytes and other epithelial cells, monocytes, and fibroblasts (icIL-1Ra). An additional 16-kDa intracellular isoform of IL-1Ra exists in neutrophils, monocytes, and hepatic cells. Both of the major isoforms of IL-1Ra are transcribed from the same gene through the use of alternative first exons. The production of IL-1Ra is stimulated by many substances including adherent IgG, other cytokines, and bacterial or viral components. The tissue distribution of IL-1Ra in mice indicates that sIL-1Ra is found predominantly in peripheral blood cells, lungs, spleen, and liver, while icIL-1Ra is found in large amounts in skin. Studies in transgenic and knockout mice indicate that IL-1Ra is important in host defense against endotoxin-induced injury. IL-1Ra is produced by hepatic cells with the characteristics of an acute phase protein. Endogenous IL-1Ra is produced in human autoimmune and chronic inflammatory diseases. The use of neutralizing anti-IL-1Ra antibodies has demonstrated that endogenous IL-1Ra is an important natural anti-inflammatory protein in arthritis, colitis, and granulomatous pulmonary disease. Patients with rheumatoid arthritis treated with IL-1Ra for six months exhibited improvements in clinical parameters and in radiographic evidence of joint damage. Arend et al., 16 ANN. REV. IMMUNOL. 27-55 (1998).

Yet another example of an IL-1Ra that may be expressed by the cell clone of the present invention is a recombinant human version called interleukin-117.3 Kd met-IL1ra, or Anakinra, produced by Amgen, (San Francisco, Calif.) under the name KINERET™. Anakinra has also shown promise in clinical studies involving patients with rheumatoid arthritis (Presented at the 65th Ann. Sci. Meeting of Am. College Rheumatology. Nov. 12, 2001).

In another embodiment of the invention, the polypeptide of interest expressed by the cell clone of the present invention is interleukin 12 (IL-12) or an antagonist thereof. IL-12 is a heterodimeric cytokine consisting of glycosylated polypeptide chains of 35 and 40 kD which are disulfide bonded. The cytokine is synthesized and secreted by antigen presenting cells, including dendritic cells, monocytes, macrophages, B cells, Langerhans cells and keratinocytes, as well as natural killer (NK) cells. IL-12 mediates a variety of biological processes and has been referred to as NK cell stimulatory factor (NKSF), T-cell stimulating factor, cytotoxic T-lymphocyte maturation factor and EBV-transformed B-cell line factor. Curfs et al., 10 CLIN. MICRO. REV. 742-80 (1997). Interleukin-12 can bind to the IL-12 receptor expressed on the plasma membrane of cells (e.g., T cells, NK cell), thereby altering (e.g., initiating, preventing) biological processes. For example, the binding of IL-12 to the IL-12 receptor can stimulate the proliferation of pre-activated T cells and NK cells, enhance the cytolytic activity of cytotoxic T cells (CTL), NK cells and LAK (lymphokine activated killer) cells, induce production of gamma interferon (IFN GAMMA) by T cells and NK cells and induce differentiation of naive Th0 cells into Th1 cells that produce IFN GAMMA and IL-2. Trinchieri, 13 ANN. REV. IMMUNOLOGY 251-76 (1995). In particular, IL-12 is vital for the generation of cytolytic cells (e.g., NK, CTL) and for mounting a cellular immune response (e.g., a Th1 cell mediated immune response). Thus, IL-12 is critically important in the generation and regulation of both protective immunity (e.g., eradication of infections) and pathological immune responses (e.g., autoimmunity). Hendrzak et al., 72 LAB. INVESTIGATION 619-37 (1995). Accordingly, an immune response (e.g., protective or pathogenic) can be enhanced, suppressed or prevented by manipulation of the biological activity of IL-12 in vivo, for example, by means of an antibody.

In another embodiment of the present invention, the polypeptide of interest comprises or targets an integrin. Integrins have been implicated in the angiogenic process, by which tumor cells form new blood vessels that provide tumors with nutrients and oxygen, carry away waste products, and to act as conduits for the metastasis of tumor cells to distant sites, Gastl et al., 54 ONCOL. 177-84 (1997). Integrins are heterodimeric transmembrane proteins that play critical roles in cell adhesion to the extracellular matrix (ECM) which, in turn, mediates cell survival, proliferation and migration through intracellular signaling. During angiogenesis, a number of integrins that are expressed on the surface of activated endothelial cells regulate critical adhesive interactions with a variety of ECM proteins to regulate distinct biological events such as cell migration, proliferation and differentiation. Specifically, the closely related but distinct integrins aVb3 and aVb5 have been shown to mediate independent pathways in the angiogenic process. An antibody generated against αVβ3 blocked basic fibroblast growth factor (bFGF) induced angiogenesis, whereas an antibody specific to αVβ5 inhibited vascular endothelial growth factor-induced (VEGF-induced) angiogenesis. Eliceiri et al., 103 J. CLIN. INVEST. 1227-30 (1999); Friedlander et al., 270 SCIENCE 1500-02 (1995).

In another preferred embodiment of the invention, the polypeptide of interest comprises at least one glycoprotein IIb/IIIa receptor antagonist. More specifically, the final obligatory step in platelet aggregation is the binding of fibrinogen to an activated membrane-bound glycoprotein complex, GP IIb/IIIa. Platelet activators such as thrombin, collagen, epinephrine or ADP, are generated as an outgrowth of tissue damage. During activation, GP IIb/IIIa undergoes changes in conformation that results in exposure of occult binding sites for fibrinogen. There are six putative recognition sites within fibrinogen for GP IIb/IIIa and thus fibrinogen can potentially act as a hexavalent ligand to crossing GP IIb/IIIa molecules on adjacent platelets. A deficiency in either fibrinogen or GP IIb/IIIa a prevents normal platelet aggregation regardless of the agonist used to activate the platelets. Since the binding of fibrinogen to its platelet receptor is an obligatory component of normal aggregation, GP IIb/IIIa is an attractive target for an antithrombotic agent.

Results from clinical trials of GP IIb/IIIa inhibitors support this hypothesis. A Fab fragment of the monoclonal antibody 7E3, which blocks the GP IIb/IIIa receptor, has been shown to be an effective therapy for the high risk angioplasty population. It is used as an adjunct to percutaneous transluminal coronary angioplasty or atherectomy for the prevention of acute cardiac ischemic complications in patients at high risk for abrupt closure of the treated coronary vessel. Although 7E3 blocks both the IIb/IIIa receptor and the $\alpha_v\beta_3$ receptor, its ability to inhibit platelet aggregation has been attributed to its function as a IIb/IIIa receptor binding inhibitor. The IIb/IIIa receptor antagonist may be, but is not limited to, an antibody, a fragment of an antibody, a peptide, or an organic molecule. For example, the target-binding moiety may be derived from 7E3, an antibody with glycoprotein IIb/IIIa receptor antagonist activity. 7E3 is the parent antibody of c7E3, a Fab fragment known as abciximab, known commercially as REOPRO® produced by Centocor, Inc. (Malvern, Pa.). Abciximab binds and inhibits the adhesive receptors GPIIb/IIIa and $\alpha_v\beta_3$, leading to inhibition of platelet aggregation and thrombin generation, and the subsequent prevention of thrombus formation. U.S. Pat. Nos. 5,976,532, 5,877,006, 5,770,198; Coller, 78 THROM HAEMOST. 730-35 (1997); JORDAN ET AL., in ADHESION RECEPTORS AS THERAPEUTIC TARGETS 281-305 (Horton, ed. CRC Press, New York, 1996); Jordan et al., in NEW THERAPEUTIC AGENTS IN THROMBOSIS & THROMBOLYSIS (Sasahara & Loscalzo, eds. Marcel Kekker, Inc. New York, 1997).

Additionally, the glycoprotein IIb/IIIa receptor antagonist expressed by the cell clone of the present invention may comprise a thrombolytic. For example, the thrombolytic may be tPA, or a functional variation thereof. RETAVASE®, produced by Centocor, Inc. (Malvern, Pa.), is a variant tPA with a prolonged half-life. In mice, the combination of Retavase and the IIb/IIIa receptor antagonist c7E3 Fab markedly augmented the dissolution of pulmonary embolism. See Provisional Patent Application Ser. No. 60/304,409.

Alternatively, the method of the present invention can be used to identify cell clones secreting non-peptide molecules. For example, natural signaling molecules are endogenous compounds which chemically effect receptors. Many pharmacologically active drugs act on the cellular receptor level by either mimicking the action of a natural signal molecule (agonist) or by blocking the action of the natural signal molecule (antagonist). As a non-limiting example, tirofiban hydrochloride is a non-peptide antagonist of the platelet glycoprotein IIb/IIIa receptor that inhibits platelet aggregation. See U.S. Pat. No. 6,117,842, issued Sep. 12, 2000. Tirofiban is commercially available as AGGRASTAT® from Merck & Co., Inc., (Whitehouse Station, N.J.), manufactured by Baxter Healthcare Corp. (Deerfield, Ill.) and Ben Venue Labs. (Bedford, Ohio). The structure of Tirofiban is illustrated below where X is or contains a functional group capable of forming the ΨAb structure. The position of X is selected at any of those aromatic sites on the molecule for which substitution will retain some activity of the parent structure, and is not limited to that position depicted in the drawing.

(such as Gentamicin), Macrolides (such as Erythromycin), Fluoroquinolones, Metronidazole, Sulfonamides, Tetracyclines, Trimethroprim, and Vancomycin. Antifungal agents include, but are not limited to Amphotericin, Fluconazole, Flucytosine, Itraconazole, and Ketoconazole. Antiparasitic agents include, but are not limited to, Ivermectin, Mebendazole, Mefloquine, Pentamidine, Praziquantel, Pyrimethamine, and Quinine. Antiviral agents include, but are not limited to, Acyclovir, Amantadine, Didanosine, Famciclovir, Foscarnet, Ganciclovir, Rimatandine, Stavudine, Zalcitabine, and Zidovudine. Antimycobacterial agents include, but are not limited to, Isoniazid, Rifampin, Streptomycin, Dapsone. SANFORD ET AL., GUIDE TO ANTIMICROBIAL THERAPY (25th ed., Antimicrobial Therapy, Inc., Dallas, Tex. 1995).

The method of the present invention may also be used to identify and/or characterize cell clones expressing a particular antigen. Antigens, in a broad sense, may include any molecule to which an antibody, or functional fragment thereof, binds. Such antigens may be pathogen derived, and be associated with either MHC class I or MHC class II reactions. These antigens may be proteinaceous or include carbohydrates, such as polysaccharides, glycoproteins, or lipids.

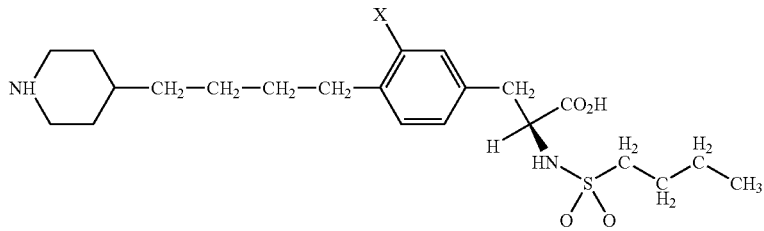

35

The polypeptide of interest expressed by the cell clone of the present invention also include receptors or fragments thereof, and activated receptors, i.e., recombinant peptides that mimic ligands associated with their corresponding receptors, or fragments thereof. These complexes may mimic activated receptors and thus affect a particular biological activity. An example of activated-receptor moieties concerns the peptido mimetics of the erythropoietin (Epo) receptor. By way of background, the binding of Epo to the Epo receptor (EpoR) is crucial for production of mature red blood cells. The Epo-bound, activated EpoR is a dimer. See, e.g., Constantinescu et al., 98 PNAS 4379-84 (2001). In its natural state, the first EpoR in the dimer binds Epo with a high affinity whereas the second EpoR molecule binds to the complex with a low affinity. Bivalent anti-EpoR antibodies have been reported to activate EopR, probably by dimerization of the EpoR. Additionally, small synthetic peptides, that do not have any sequence homology with the Epo molecule, are also able to mimic the biologic effects of Epo but with a lower affinity. Their mechanism of action is probably also based on the capacity to produce dimerization of the EpoR. Hence, an embodiment of the present invention provides for a method of identifying and characterizing cell clones expressing an activated EpoR mimetic.

In another preferred embodiment, the method of the present invention may be used to identify cell clone that secrets antimicrobial agents or portions thereof, which include antibacterial agents, antivirals agents, antifungal agents, antimycobacterial agents, and antiparasitic agents. Antibacterials include, but are not limited to, Beta-lactams (such as Penicillins and Cephalosporins), Aminoglycosides Carbohydrate and lipid antigens are present on cell surfaces of all types of cells, including normal human blood cells and foreign, bacterial cell walls or viral membranes. Nucleic acids may also be antigenic when associated with proteins, and are hence included within the scope of antigens encompassed in the present invention. See SEARS, IMMUNOLOGY (W. H. Freeman & Co. and Sumanas, Inc., 1997), available on-line at http://www.whfreeman.com/immunology. For example, antigens may be derived from a pathogen, such as a virus, *bacterium, mycoplasm*, fungus, parasite, or from another foreign substance, such as a toxin. Such bacterial antigens may include or be derived from *Bacillus anthracis, Bacillus tetani, Bordetella pertusis; Brucella* spp., *Corynebacterium diphtheriae, Clostridium botulinum, Clostridium perfringens, Coxiella burnetii, Francisella tularensis, Mycobacterium leprae, Mycobacterium tuberculosis, Salmonella typhimurium, Streptocccus pneumoniae, Escherichia coli, Haemophilus influenzae, Shigella* spp., *Staphylococcus aureus, Neisseria gonorrhoeae, Neisseria meningiditis, Treponema pallidum, Yersinia pestis, Vibrio cholerae*. Often, the oligosaccharide structures of the outer cell walls of these microbes afford superior protective immunity, but must be conjugated to an appropriate carrier for that effect.

Viruses and viral antigens that are within the scope of the current invention include, but are not limited to, HBeAg, Hepatitis B Core, Hepatitis B Surface Antigen, Cytomegalovirus B, HIV-1 gag, HIV-1 nef, HIV-1 env, HIV-1 gp41-1, HIV-1 p24, HIV-1 MN gp120, HIV-2 env, HIV-2 gp 36, HCV Core, HCV NS4, HCV NS3, HCV p22 nucleocapsid, HPV LI capsid, HSV-1 gD, HSV-1 gG, HSV-2 gG, HSV-II, Influenza A (H1N1), Influenza A (H3N2), Influenza B, Parainfluenza Virus Type 1, Epstein Barr virus capsid antigen, Epstein Barr virus, *Poxyiridae Variola major, Poxyiridae Variola minor, Rotavirus, Rubella* virus, Respiratory Syncytial Virus, Surface Antigens of the Syphilis spirochete, Mumps Virus Antigen, *Varicella zoster* Virus Antigen and *Filoviridae*.

Other parasitic pathogens such as *Chlamydia trachomatis, Plasmodium falciparum,* and *Toxoplasma gondii* may also be included in the scope of the present invention. Numerous bacterial and viral, and other microbe-generated antigens are available from commercial suppliers such as Research Diagnostics, Inc. (Flanders, N.J.).

Toxins, toxoids, or antigenic portions of either, within the scope of the present invention include those produced by bacteria, such as diphteria toxin, tetanus toxin, botulin toxin and enterotoxin B; those produced by plants, such as Ricin toxin from the castor bean *Ricinus cummunis*. Mycotoxins, produced by fungi, that may serve in the present invention include diacetoxyscirpenol (DAS), Nivalenol, 4-Deoxynivalenol (DON), and T-2 Toxin. Other toxins and toxoids produced by or derived from other organisms may also be included in the scope of the present invention.

Vectors

In a preferred embodiment, the cell clone of the present invention expresses at least one polypeptide of interest in detectable amount. A variety of mammalian expression vectors may be used to express the polypeptide of interest in the cell clone of the present invention. Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenylic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference).

Suitable vectors are readily apparent to the skilled artisan. For example, commercially available mammalian expression vectors that may be suitable for the present invention include, but are not limited to, pMAMneo (Clontech, Palo Alto, Calif.), pcDNA3 (Invitrogen, Carlsbad, Calif.), pMClneo (Stratagene, La Jolla, Calif.), pXT1 (Stratagene, La Jolla, Calif.), pSG5 (Stratagene, La Jolla, Calif.), EBO-pSV2-neo (ATCC, Manassas, Va., ATCC No. 37593), pBPV-[(8-2) (ATCC No. 37110), pdBPV-MMTneo(342-12) (ATCC No. 37224), pRSVgpt (ATCC No.] 37199), pRSVneo (ATCC No. 37198), pSV2-dhfr (ATCC No. 37146), pUCTag (ATCC No. 37460), and 17D35 (ATCC No. 37565).

The nucleic acid encoding at least one polypeptide of interest may be introduced by one of several methods well known in the art, including but not limited to, transfection, including but not limited to, calcium phosphate transfection, DEAE-dextran mediated transfection and cationic lipid-mediated transfection, electroporation, sonication, transduction, transformation, and viral infection. Such methods are described in the art, see, e.g., Samsrook et al., Molecular Cloning: a Lab Manual, 3$^{rd}$ edition, Cold Spring Harbor, N.Y. (2001); Ausubel et al., Current Protocols in Molecular Biology, John Wiley & Sons, Inc., NY, N.Y. (1987-2003).

Host Cell Lines

The host cells in the present invention can be at least one selected from prokaryotic or eukaryotic cells, or fusion cells thereof, e.g., but not limited to, bacterial cells, blue-green algae cells, yeast cells, silk worm cells, plant cells, insect cells, amphibian cells, fish cells, avian cells, mammalian cells, or any derivative, immortalized or transformed cell thereof. Preferably, the cells are eukaryotic cells. More preferably, the cells are mammalian cells.

In a preferred embodiment, suitable cell lines that can be used according to the present invention include any transformed or immortalized mammalian cell line. The host cell can optionally be at least one selected from myeloma cells, such as but not limited to Sp2/0, NSO, NS1, CHO, BHK, Ag653, P3X63Ag8.653 (ATCC Accession Number CRL-1580) and SP2/0-Ag14 (ATCC Accession Number CRL-1851), COS-1(e.g., ATCC CRL-1650), COS-7 (e.g., ATCC CRL-1651), HEK293, BHK21 (e.g., ATCC CAL-10), CHO (e.g., ATCC CRL-1610, CHO DXB-11, CHO DG44), BSC-1 (e.g., ATCC CAL-26), HepG2, 293, HeLa, NIH 3T3, CDS-1, CDS-7, NIH 273, or lymphoma cells, or any derivative, immortalized or transformed cell thereof. A preferred cell line is C463A, which is derived from Sp2/0 and can be used as a transfection host. See U.S. application 60/339,428, WO2003051720 and WO993052964, herein entirely incorporated by reference.

As used herein, the term "colony" or "colonies" may be defined by the number of cells or total diameter, which is determined by the researcher. Typically, a colony has at least 40 or 50 cells, although sometimes as few as 30 cells or less. The incubation period required for a given cell type to reach the critical size or number of cells to be called a colony varies between cell types, but typically requires an incubation period of between 7-14 days, with longer periods needed if the cell growth is slow. If diameter is used as the defining criterion, a colony is typically defined as being 10-50 microns, such as 10-20, 20-30, 30-40, 40-50 microns or any range or value therein.

Media

Appropriate culture media and conditions for the above-described host cells are well known in the art. Numerous types of growth media are commercially available, such as but not limited to Iscove's Modified Medium, Dulbecco's Modified Eagel Medium, RPMI, Ham's F10, Ham's F12, Minimum Essential Medium and alpha medium etc. In addition to growth media, cells cultured in vitro require many growth factors to either promote growth or maintain viability. The growth factors may be supplied by for example, 5-10% fetal bovine serum (FBS) to promote cell growth and protein production. However, cell growth media include serum-free (containing 0-0.5% serum) or serum-reduced (containing 0.5-5.0% serum) media.

To support the growth of mammalian cells, a variety of components, e.g. but not limited to, glutamine, glucose, vitamins, amino acids and growth factors, may be included in the culture media. Trace elements such as zinc, iron, selenium, copper, molybdenum, and manganese etc. are important for cloning and continuous passage of mammalian cells in stringent conditions of serum-free media. Alternatively, cell growth media include deficient media, where one or more nutrients are deleted. Growth media also include specialty media which are designed to promote growth of specific cell types.

Growth media may include additional antibiotics, attachment and matrix factors which are usually added to facilitate attachment and spreading of many types of anchorage dependent cells. Buffers may also be added to growth media in order to maintain pH levels. Such buffers may include but are not limited to MOPS, HEPES, sodium phosphate, potassium phosphate, Tris or other known buffers.

In addition, chemically defined media (CDM) can be used in the present invention. CDM provide certain compounds, amino acids, lipids, carbohydrates, trace elements and/or vitamins and exclude the use of non-defined animal derived raw materials, e.g. but not limited to, primatone, albumin and Excyte™, as well as other similar materials derived from serum or other animal derived proteins or products. Such media allow the growth of cells to provide commercially useful amounts of the desired proteins expressed in such cell cultures. Some of the advantages of CDM include but not limited to better protein producing, commercially suitable, cost-effective, and/or pose reduced regulatory concerns for proteins produced in cell lines grown therein. For detailed compositions and formulations of CDM, see e.g. but not limited to WO2002066603, herein entirely incorporated by reference.

As used herein the term "semi-solid medium" refers to a cell growth medium that does not provide a solid substrate to which cells can attach, and that is sufficiently viscous such that cells added to the semi-solid medium are suspended therein, and are thereby prevented from sinking through the semi-solid medium and contacting, and attaching to, the inner surface of the container within which the semi-solid medium is dispensed. Because a semi-solid medium holds the cells in situ, it permits continuous observation of a single cell or individual colony.

Semi-solid media useful in the practice of the present invention typically include a gelatinization agent dissolved in an aqueous medium in an amount of from 0.1% to 5.0% (w/v), such as 0.1-0.5%, 0.5-1.0%, 1.0-1.5%, 1.5-2.0%, 2.0-2.5%, 2.5-3.0%, 3.0-3.5%, 3.5-4.0%, 4.0-4.5%, 4.5-5.0% or any range or value therein. Preferred semi-solid media are those capable of sustaining growth of cells. Non-limiting examples of gelatinization agents include agar, agarose, methylcellulose, or any other polymer suitable for the purpose of the present invention.

One category of the semi-solid media forms a liquid at temperatures above room temperature or above the temperature required to incubate the cells, and forms a semi-solid or gel when at room temperature or the temperature at which the cells are incubated. For example, agar is a class of polysaccharide complex generally defined as a dried mucilaginous substance extracted from the agarocytes of algae of the Rhodophyceae. Agar-producing genera include but not limited to, *Gelidium, Gracilaria, Acanthopeltis, Ceramim, Pterocladia* etc. Agar melts at about 100° C. and solidifies into a gel at about 40° C. It is not digested by most bacteria. Agarose is a modified agar, whereby sugars, methyl groups, and other chemical groups are chemically bonded to agar in order to enhance desired physical properties, such as low gelling temperature.

Additional gelatinization agents include, but are not limited to a wide variety of polymers, including proteins and their derivatives, may be used as semi-solid matrices in the present invention. Matrigel®, collagen or gelatin, or other similar materials may also be used as the semi-solid matrix.

Methylcellulose (cellulose methyl ether) belongs to a group of compounds known as cellulose ethers. The cellulose ethers are manufactured by a reaction of purified cellulose with alkylating reagents (methyl chloride) in presence of a base, typically sodium hydroxide and an inert diluent. The addition of the base in combination with water activates the cellulose matrix by disrupting the crystalline structure and increasing the access for the alkylating agent and promotes the etherification reaction. This activated matrix is called alkali cellulose. Methylcellulose is prepared from wood pulp or chemical cotton by treatment with alkali and methylation of the alkali cellulose with methyl chloride that adds methyl ether groups. The reaction can be characterized as:

$$R_{cell}OH:NaOH+CH_3Cl \rightarrow R_{cell}OCH_3+NaCl$$

One significant property of methylcellulose is its reversible thermal gelation: it is soluble in cold water but insoluble in hot water. An aqueous solution is best prepared by dispersing the granules in hot (but not boiling) water with stirring and chilling to +5° C. Presence of inorganic salts increases the viscosity. At room temperature, methylcellulose solution is stable and stays in semi-solid gel form. It supports mammalian cell growth when mixed with the proper growth medium. The viscosity of methylcellulose prevents aggregation of the cells. In one embodiment, the final concentration of methylcellulose in the semi-solid capture medium is 1%. In another embodiment, the final concentration is around 0.7%. Less methylcellulose in the medium allows better diffusion of the capture molecule and accordingly increases the detection sensitivity.

Alternatively, premixed methylcellulose based semi-solid media are commercially available, such as but not limited to, ClonaCell™-TCS and MethCult™ media (StemCell Technologies), Stemline™ methylcellulose media (Sigma-Aldrich, St. Louis, Mo.).

Addition of methylcellulose is traditionally used when culturing erythroid progenitor cells. The application of methylcellulose for screening and selection of antibiotic resistant clones has been described and commercially available, e.g. see Technical Manual ClonalCell™-TCS, Transfected Cell Selection Kit, Stemcell Technologies.

Capture Molecule

As used herein the term "the capture molecule" refers to a molecule that can bind or react with the polypeptide of interest and form a halo-like precipitate visible under a microscope. Potential capture molecule can be but are not limited to, receptor or ligand of the polypeptide of interest, antibody or antigen against the polypeptide of interest etc. Accordingly, as used herein the term "the capture medium" refers to the semi-solid cell growth medium with at least one capture molecule incorporated.

The capture molecule can be directly added to the semi-solid medium, either by mixing it with the medium before pouring the plates, or by overlaying the pored plates with a layer of medium containing the capture molecule. The capture molecule can be radio-labeled, fluorescent-labeled or labeled by any other methods known in the art to facilitate the detection of precipitate. For example, a capture antibody is fluorescent-labeled and added to the semi-solid medium. Upon binding to the polypeptide of interest (i.e., the antigen), the antigen-antibody complex can be easily observed under fluorescent microscope and the cell clone expressing the polypeptide of interest can be identified.

In one embodiment, the capture molecule is an antibody against the polypeptide of interest. The final concentration of the capture antibody used can be 0.0225-0.225 mg/ml, such as 0.0225-0.045, 0.045-0.0675, 0.0675-0.09, 0.09-0.1125, 0.1125-0.135, 0.135-0.1575, 0.1575-0.18, 0.18-0.2025, 0.2025-0.225 mg/ml, or any range or value therein. In a preferred embodiment, the final concentration of the capture antibody is 0.1125 mg/ml. In general, lower concentration of the capture molecule increases the detection sensitivity by selecting cell clones expressing the polypeptide of interest at higher levels.

In one variation of the aforedescribed methods, this strategy is used to screen a nucleic acid library, such as a cDNA library, that encodes a population of candidate protein molecules that are being screened for their ability to bind or to react with the capture molecule and form precipitate. The cDNA library is introduced into cells by means well known in the art, such as by transfection or transduction. The cells are cultured in a semi-solid medium, preferably a methylcellulose based medium, in which a capture molecule is added. The colonies around which a precipitated halo is observed can be isolated and further studied. The foreign DNA can be retrieved from such colonies to identify and isolate the capture binding/interacting molecule that was responsible for the formation of the precipitate halo.

Isolating Polypeptide of Interest

In one embodiment, after the cell clone being identified, it is harvested and expanded in culture and the polypeptide of interest is isolated therefrom using techniques well established in the art. The polypeptide of interest preferably is recovered from the culture medium as a secreted polypeptide. As a first step, the culture medium is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration etc. A protease inhibitor such as phenyl methyl sulfonyl fluoride (PMSF) also may be useful to inhibit proteolytic degradation during purification. Additionally, the polypeptide of interest can be fused in frame to a marker sequence, such as but not limited to a hexahistidine (HA) tag, which allows for purification of the polypeptide of interest.

The methods of the present invention are also useful in identifying cell clones expressing G-protein coupled receptors (GPCRs) and other transmembrane proteins. These proteins may be purified as part of a membrane fraction or purified from the membranes by methods known in the art.

Advantage

In the present invention, cells producing the polypeptide of interest can be identified by reference to the formation of halo. It will be clear to the skilled artisan that one of the benefits of the present invention is that it eliminates intermediate steps normally required in conventional screening methods, such as ELISA. In addition, high level producers can be identified by reference to the timing of the halo formation and the size of the formed halo. Therefore, the present invention provides a simple yet powerful qualitative screening method in contrast to conventional methods, such as ELISA, which are largely quantitative. Accordingly, the method of the present invention can be used as the primary screening method to examine large number of cells and is less labor-intensive and less time-consuming.

It will also be clear to the skilled artisan that this method can be used in robotic screening and in protocols for high throughput selection of cells producing high levels of a product of interest.

A preferred embodiment of the present invention is described by reference to the following examples, which are provided by way of illustration and are not intended as limiting. In this embodiment exemplified below, selection can be visually monitored by the immunoprecipitate (halo) formed between the chimeric anti-TNF antibody cA2 and the capture antibody rabbit anti-human IgG (H&L), while the production level of cA2 correlates with the size of the halo.

Example 1

Preparation of Methylcellulose Based Semi-Solid Capture Medium with Capture Antibody Pre-made semi-solid matrix (4000 cps) containing methylcellulose in growth medium such as IMDM, EMDM, CD CHO, CD Hybridoma are commercially available. For example, Methocult from StemCell Technologies was used in the following experiments.

The semi-solid capture medium was prepared by adding 1 ml capture antibody (2 mg/ml) to 13 ml methylcellulose medium. Antibiotic reagent and cell suspension were added to the mixture along with FBS, L-glutamine and additional growth medium to make 20 ml of final volume. In this example, the final concentration of the components are 1% methylcellulose, 30% FBS and 2 mM L-glutamine. It is readily understood that other concentrations suitable for the specific cell line are within the scope of this invention.

This working mixture was placed in a proper container (such as a 50 ml conical centrifuge tube) and mixed or vortexed vigorously for 30 seconds. After mixing, the tubes sat at room temperature for 5-10 minutes to allow air bubbles to disappear. The 20 ml of cells in the capture medium was evenly dispensed into a 6-well plate. The plate was incubated in a 37° C. $CO_2$ incubator without disturbance for 7 to 10 days. The plates were then removed for examination.

The sensitivity of this assay can be optimized by changing the concentration of capture antibody and the amount of methylcellulose used to make the semi-solid capture meidum. Combination of lower capture antibody concentration and less methylcellulose routinely result in better detection sensitivity.

Example 2

Transfection and Initial Selection of Myeloma Cells Using Antibiotics

Murine myeloma Sp2/0 derived cell line C463A was transfected with chimeric anti-TNF antibody cA2 expression plasmids by electroporation as described by Knight et al.

In brief, the expression plasmid for cA2 heavy chain was linearized by digestion with XhoI and the expression plasmid for cA2 light chain was linearized using KpnI restriction enzyme. $10 \times 10^6$ C463A cells were transfected with about 10 µg of linearized plasmid by electroporation (200V and 1180 uF). Following the electroporation, the cells were plated in T-75 flasks for 72 hours. After recovery, cells were selected with 0.5 µg/ml mycophenylic acid for 2-5 passages.

Example 3

Colony Formation and Halo Detection in Methylcellulose Based Semi-Solid Capture Medium Transfected cells from the antibiotic selected culture were plated in methylcellulose based semi-solid capture medium in 6-well plates at $1-3 \times 10^3$ cells per well. The rabbit anti-human IgG (H&L) antibody was purchased from Jackson ImmunoResearch Laboratories, Inc. This capture antibody recognizes the chimeric anti-TNF cA2 mAb used in the experiment and has been used in Nephelometry for IgG quantitation.

In this assay, the capture antibody was incorporated to the methylcellulose based semi-solid capture medium at the final concentration of 1 mg/ml. The cultures in semi-solid methylcellulose capture medium were incubated at 37° C., 5% $CO_2$ and >95% humidity without disturbance for 7-10 days before examination for colony and precipitate halo formation. The multiplication of cells was observed within 20 to 24 hours after plating and colonies were formed within 10 days.

Precipitates were found around cells in about two days. The precipitate became halo-like under a phase microscope in about 7 to 8 days. Selection of colonies with distinct halo was done no later than day 12. Single colonies were picked up carefully under a microscope and expanded in CD hybridoma growth medium (Invitrogen) for studying cell growth and IgG production.

Two negative control experiments were performed in this experiment. One is host cell line C463A in methylcellulose medium with capture antibody. The other one is cA2 producing C463A cells in methylcellulose medium without capture antibody. No halo-like structure was found in either of the negative controls.

Example 4

Selection of Clones Through Correlation Between the Halo Size and the Level of IgG Production Previously, some of the major obstacles to use agarose based semi-solid growth medium for screening high production cell lines include the difficulty to observe the halo formation even under the microscope as well as the poor correlation between the size of halos and the actual protein production. The new method improves the halo formation, which makes the correlation of halo size to protein production more accurate and reliable.

To correlate halo size to protein production, 20 colonies from each of the following categories were picked and grown in 24-well plates with 1 ml of IMDM+5% FBS growth medium:
 large halo: the width of the halo is equal to or greater than the radius of the colony that the halo surrounds;
 small halo: the width of halo is equal or less than half of the radius of the colony that the halo surrounds; and
 haloless: no surrounding halo was observed.

Colonies from each category were grown for 12 days. The supernatant of these cultures was then collected for IgG quantitation by a nephlometer. IgG titers from different sizes of halo were then analyzed statistically (T test and F test). The results (Table 1) clearly showed a positive correlation between the halo size and the IgG production. The confidence level of obtaining high expressing clones using halo size was above 95%.

TABLE 5

Correlation between halo size and OG titer (mg/ml) in 5% FBS

| Halo Size | | Large | Small | Zero |
|---|---|---|---|---|
| OG Titer (mg/L) | 1 | 48.7 | 20.72 | 30.16 |
| | 2 | 47.25 | 5.33 | 30.56 |
| | 3 | 26.93 | 26.33 | 18.13 |
| | 4 | 33.41 | 19.41 | 17.37 |
| | 5 | 34.55 | 37.4 | 7.02 |
| | 6 | 34.26 | 29.1 | 23.14 |
| | 7 | 33.41 | 19.59 | 4.12 |
| | 8 | 35.4 | 42.29 | 18.72 |
| | 9 | 13.81 | 27.36 | 22.94 |
| | 10 | 22.37 | 22.37 | 22.71 |
| | 11 | 44.04 | 23.38 | 3.43 |
| | 12 | 52.02 | 16.2 | 4.68 |
| | 13 | 54.44 | 26.64 | 4.43 |
| | 14 | 26.93 | 26.64 | 2.99 |
| | 15 | 30.84 | 23.35 | 5.76 |
| | 16 | 34.83 | 23.23 | 3.23 |
| | 17 | 22.37 | 22.17 | 7.39 |
| | 18 | 33.69 | 31.98 | 19.56 |
| | 19 | 47.84 | 49.62 | 4.56 |
| | 20 | 40.27 | 10.7 | |
| | Average | 35.9 | 25.2 | 13.2 |

Example 5

Primary Screening for High IgG Producing Clones

Murine myeloma cells Sp2/0 or NSO were transfected with plasmids encoding an antibody against human IL-13 by electroporation as previously described in Example 2. Transfected cells from the antibiotic selected culture were plated in methylcellulose based semi-solid capture medium. After 8-14 days, colonies with halos were observed and picked into suitable growth medium. The titers of spent culture from representative transfectants in shake flasks are consistently higher than those of transfectants identified by ELISA. For example, the titer in shaker flask is in the range of 33-100 µg/ml for transfected Sp2/0 cells, and 55-108 µg/ml for transfected NSO cells.

Example 6

Subcloning of High IgG Producer

It is well known in the art that if the transfected cells have been in continuous culture for a long time, or the cells in culture are not derived from a single cell clone, they may need to be recloned. The present invention also provides a method to rapidly achieve this goal.

For cells expressing chimeric anti-TNF cA2 mAb, several clones screened by halo assay produced IgG greater than 180 ug/ml in IMDM derived medium while parental cells (before subcloning) routinely produced 120 ug/ml in the same condition. When cultured in CD hybridoma medium, greater than 80 ug/ml IgG titers were observed.

It will be clear that the invention can be practiced otherwise than as particularly described in the foregoing description and examples. Numerous modifications and variations of the present invention are possible in light of the above teachings and, therefore are within the scope of the appended claims.

What is claimed is:

1. The method for selecting eukaryotic clones highly expressing a polypeptide of interest from a population of eukaryotic cells expressing said polypeptide of interest comprising:
    (a) culturing said population of eukaryotic cells on a semi-solid culture medium;
    (b) contacting said population of cultured eukaryotic cells with a capture molecule that interacts with said polypeptide of interest, wherein the concentration of said capture molecule is between about 0.2 and 2.0 mg/ml, and said capture molecule comprises a detectable label;
    (c) incubating said population of cultured eukaryotic cells expressing said polypeptide of interest with said capture molecule for a period of time;
    (d) measuring the relative size of haloes produced by said detectable label following interaction of said polypeptide of interest with said capture molecule and wherein high expressing eukaryotic clones have a halo with a width that is equal to, or greater than, the radius of a eukaryotic cell clone lacking a halo; and
    (e) selecting at least one of said high expressing eukaryotic cell clones from said population of said eukaryotic cells.

2. The method according to claim 1, wherein said capture molecule is an antibody or a polypeptide binding fragment thereof.

3. The method according to claim 1, wherein said detectable label is selected from the group consisting of: a chemical label, a biological label, a fluorescent label and a radioactive label.

4. The method according to claim 1, wherein the semi-solid culture medium comprises a gelatinization agent comprising cellulose or agar.

5. The method according to claim 1, wherein said eukaryotic cells are selected from the group consisting of: mammalian cells, yeast cells and insect cells.

6. The method according to claim 5, wherein said mammalian cells are selected from the group consisting of: COS-1, COS-7, HEK293, HK21, CHO, BSC-1, HepG2, 653, SP2/0, 293, NS0, DG44 CHO, CHO K1, HeLa, myeloma, and lymphoma cells, or any derivative, immortalized or transformed cells thereof.

7. The method according to claim 1, wherein said polypeptide of interest is a soluble polypeptide.

8. The method according to claim 1, wherein said polypeptide of interest is an immunoglobulin or at least a portion thereof.

9. The method according to claim 1, wherein the capture molecule is selected from the group consisting of a portion of a ligand wherein the portion binds to the polypeptide of interest, a portion of a receptor wherein the portion of said receptor binds to the polypeptide of interest, and an antibody that binds to the polypeptide of interest.

10. The method according to claim 9, wherein said capture molecule is an antibody that binds said polypeptide of interest.

11. The method according to claim 1, wherein the cells are myeloma cells, said polypeptide of interest is an immunoglobulin, the capture molecule is an antibody against the immunoglobulin, and the semi-solid culture medium is methylcellulose based.

12. The method according to claim 1, wherein the concentration of said capture molecule is 1.0 mg/ml.

13. The method according to claim 1, wherein said polypeptide of interest is at least one member selected from the group consisting of: a growth factor, a cytokine, a blood protein, a neurotransmitter, and a pharmacologically active peptide, or any portion or derivative thereof.

14. The method according to claim 1, wherein said polypeptide of interest is an antagonist of at least one member selected from the group consisting of: growth factors, cytokines, blood proteins, neurotransmitters, and pharmacologically active peptides, or portions or derivatives thereof.

15. The method according to claim 14, wherein said antagonist is at least one member selected from the group consisting of: an antibody, an antibody fusion, and an antibody fragment, or any portion or derivative thereof.

* * * * *